United States Patent
Joye et al.

(10) Patent No.: US 6,955,174 B2
(45) Date of Patent: *Oct. 18, 2005

(54) CRYOTHERAPY METHOD FOR DETECTING AND TREATING VULNERABLE PLAQUE

(75) Inventors: James Joye, Saratoga, CA (US); Kristine Tatsutani, Cupertino, CA (US); Joseph J. Williams, Sacramento, CA (US)

(73) Assignee: Uryovascular Systems, Inc., Los Gatos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/387,347

(22) Filed: Mar. 11, 2003

(65) Prior Publication Data

US 2004/0002749 A1 Jan. 1, 2004

Related U.S. Application Data

(63) Continuation-in-part of application No. 09/641,462, filed on Aug. 18, 2000, now Pat. No. 6,602,246.

(51) Int. Cl.[7] .............................................. A61B 18/18
(52) U.S. Cl. ......................................... 128/898; 606/21
(58) Field of Search ...................... 606/20–27; 128/898

(56) References Cited

U.S. PATENT DOCUMENTS

| | | |
|---|---|---|
| 3,901,241 A | 8/1975 | Allen, Jr. |
| 4,336,691 A | 6/1982 | Burstein et al. |
| 4,754,752 A | 7/1988 | Ginsburg et al. |
| 5,019,075 A | 5/1991 | Spears et al. |
| 5,041,089 A | 8/1991 | Mueller et al. |

FOREIGN PATENT DOCUMENTS

| | | |
|---|---|---|
| WO | WO 91/05528 | 5/1991 |
| WO | WO 98/38934 | 11/1998 |
| WO | WO 01/64145 A1 | 9/2001 |
| WO | WO 02/04042 A2 | 1/2002 |
| WO | WO 02/07625 A2 | 1/2002 |
| WO | WO 02/015807 A1 | 2/2002 |
| WO | WO 02/38065 A1 | 5/2002 |

OTHER PUBLICATIONS

Casscells, W., et al. *The Vulnerable Atherosclerotic Plaque: Understanding, Identification, and Modification; Chapter 13; Thermography.* Armonk, NY: Futura Publishing Company, Inc.; © 1999. pp. 231–242.

Dalager–Pedersen, S., et al. *The Vulnerable Atherosclerotic Plaque; Understanding, Identification, and Modification; Chapter 1: Coronary Artery Disease; Plaque Vulnerability, Disruption, and Thrombosis.* Armonk, NY:Futura Publishing Company, Inc.; © 1999. pp. 1–23.

Diamantopoulos, L., et al.; http://www.eurekalert.org/releases/aha–ati0041499.html, "Artery Temperatures Identify Hot Spots on Plaque that May Rupture and Trigger Heart Attack," (Release date: Apr. 20, 1999) 3 pages.

(Continued)

Primary Examiner—Michael Peffley
Assistant Examiner—Pete Vrettakos
(74) Attorney, Agent, or Firm—Townsend and Townsend and Crew LLP; Mark D. Barriah

(57) ABSTRACT

Methods, apparatus, and kits detect and/or treat vulnerable plaque of a blood vessel. A temperature differential can be sensed along a lumen surface with temperature sensors on a balloon filled with warm gas. Treatment methods include controlled and safe cryogenic cooling of vulnerable plaque to inhibit release of retained fluid within the vulnerable plaque so as to inhibit acute coronary syndrome and to help maintain patency of a body lumen.

19 Claims, 19 Drawing Sheets

U.S. PATENT DOCUMENTS

| | | | |
|---|---|---|---|
| 5,078,713 | A | 1/1992 | Varney |
| 5,092,841 | A | 3/1992 | Spears |
| 5,106,360 | A | 4/1992 | Ishiwara et al. |
| 5,147,355 | A | 9/1992 | Friedman et al. |
| 5,151,100 | A | 9/1992 | Abele et al. |
| 5,190,539 | A | 3/1993 | Fletcher et al. |
| 5,191,883 | A | 3/1993 | Lennox et al. |
| 5,196,024 | A | 3/1993 | Barath |
| 5,275,595 | A | 1/1994 | Dobak, III |
| 5,458,612 | A | 10/1995 | Chin |
| 5,486,208 | A | 1/1996 | Ginsburg |
| 5,501,681 | A | 3/1996 | Neuwirth et al. |
| 5,545,195 | A | 8/1996 | Lennox et al. |
| 5,617,739 | A | 4/1997 | Little |
| 5,644,502 | A | 7/1997 | Little |
| 5,733,280 | A | 3/1998 | Avitall |
| 5,868,735 | A * | 2/1999 | Lafontaine .................. 606/21 |
| 5,899,899 | A | 5/1999 | Arless et al. |
| 5,902,299 | A | 5/1999 | Jayaraman |
| 5,924,997 | A | 7/1999 | Campbell |
| 5,971,979 | A | 10/1999 | Joye et al. |
| 6,245,026 | B1 * | 6/2001 | Campbell et al. ........... 600/549 |
| 6,290,696 | B1 | 9/2001 | Lafontaine |
| 6,451,011 | B2 | 9/2002 | Tu |

OTHER PUBLICATIONS

Kruuv, Jack. "Survival of Mammalian Cells Exposed to Pure Hypothermia in Culture." *Advances in Molecular and Cell Biology.* (1997) 9:143–190.

Quinn, P.J. "A Lipid–Phase Separation Model of Low–Temperature Damage to Biological Membranes." *Cryobiology.* (1985) 22:128–146.

Taylor, Michael J. *Biology of Cell Survival in the Cold.* Organ Recovery Systems, Inc. & Allegheny University of Health Sciences. Greenwich, CT: JAI Press, 1996:1–64.

U.S. Appl. No. 09/203,011 filed Dec. 1, 1998 entitled: *Apparatus and Method for Cryogenic Inhibition of Hyperplasia*, Inventor(s): James Joye et al.

U.S. Appl. No. 09/344,177 filed Jun. 24, 1999 entitled: *Cryosurgical Catheter Inhibition of Hyperplasia*, Inventors(s): James Joye et al.

U.S. Appl. No. 09/510,903 filed Feb. 23, 2000 entitled: *Cryogenic Angioplasty Catheter*, Inventor(s): James Joye et al.

U.S. Appl. No. 09/511,191 filed Feb. 23, 2000 entitled: *Cryogenic Angioplasty Catheter*, Inventor(s): James Joye et al.

U.S. Appl. No. 09/268,205 filed Mar. 15, 1999 entitled: *Cryosurgical Fluid Supply*, Inventor(s): James Joye et al.

U.S. Appl. No. 09/619,583 filed Jul. 19, 2000 entitled: *Improved Safety Cryotherapy Catheter*, Inventor(s): James Joye et al.

* cited by examiner

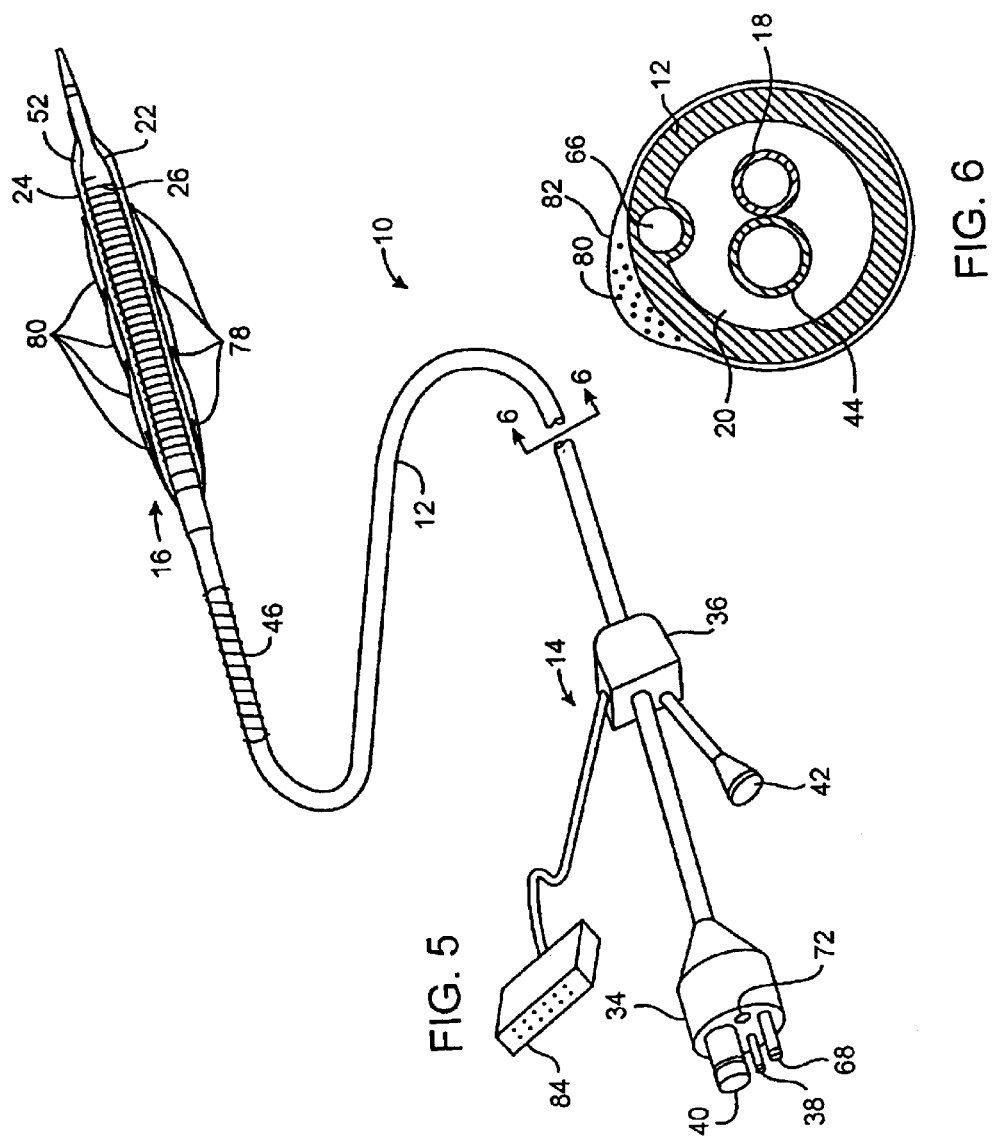

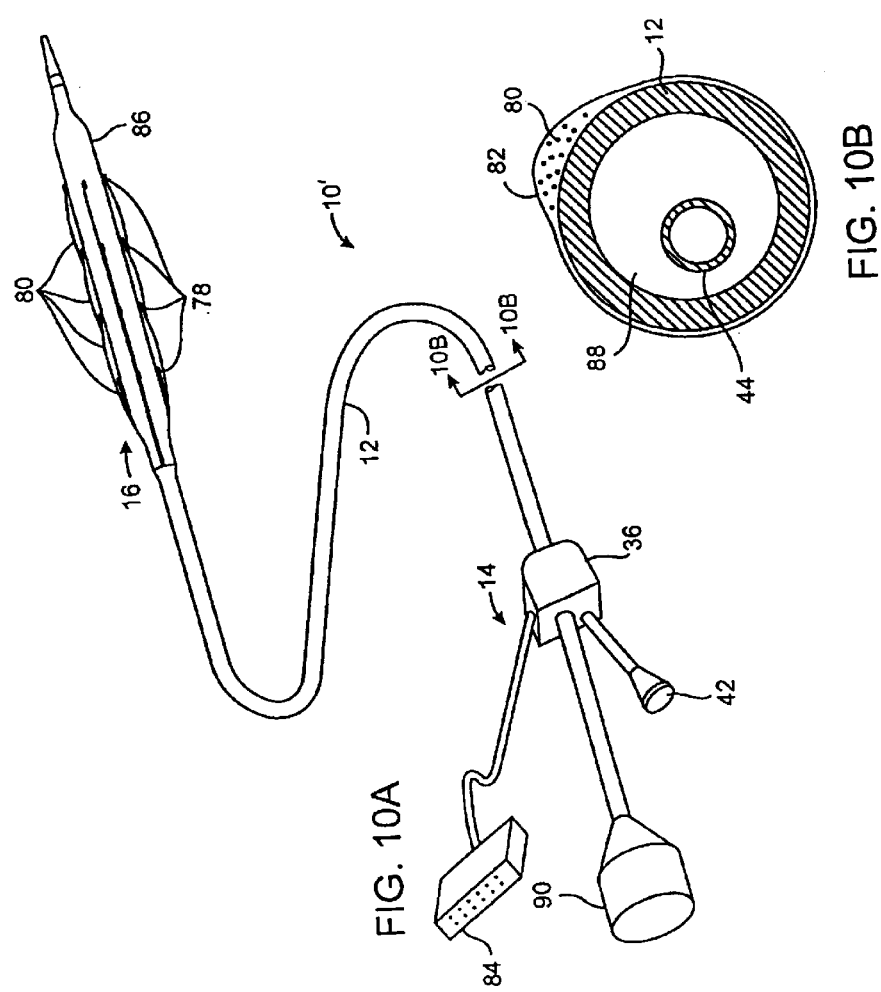

Initial Steady State Temperature Distribution

CRYOTHERAPY METHOD FOR DETECTING AND TREATING VULNERABLE PLAQUE

CROSS-REFERENCE TO RELATED APPLICATION

This is a continuation-in-part patent application which claims priority from U.S. patent application Ser. No. 09/641,462 filed now U.S. Pat. No. 6,602,246, Aug. 18, 2000, the full disclosure of which is incorporated herein by reference.

BACKGROUND OF THE INVENTION

1. Field of the Invention

The present invention relates generally to methods, apparatus, and kits for treating blood vessels. More particularly, the present invention provides methods, apparatus, and kits for identifying and/or treating a lesion. In one exemplary embodiment, the invention provides devices which are particularly useful for identification and treatment of vulnerable atherosclerotic plaque within a patient's vasculature to inhibit harmful releases within the vasculature, such as those which may be responsible for strokes or acute coronary syndromes of unstable angina, myocardial infarction, and sudden cardiac death.

Atherosclerotic plaque is present to some degree in most adults. Plaques can severely limit the blood flow through a blood vessel by narrowing the open vessel lumen. This narrowing effect or stenosis is often responsible for ischemic heart disease. Fortunately, a number of percutaneous intravascular procedures have been developed for treating atherosclerotic plaque in a patient's vasculature. The most successful of these treatments may be percutaneous transluminal angioplasty (PTA). PTA employs a catheter having an expansible distal end, usually in the form of an inflatable balloon, to dilate a stenotic region in the vasculature to restore adequate blood flow beyond the stenosis. Other procedures for opening stenotic regions include directional atherectomy, laser angioplasty, stents, and the like. Used alone or in combination, these percutaneous intravascular procedures have provided significant benefits for treatment of stenosis caused by plaque.

While treatments of stenosis have advanced significantly over the last few decades, the morbidity and mortality associated with vascular plaques have remained significant. Recent work suggests that plaque may generally fall into one of two different general types: standard stenotic plaques and vulnerable plaques. Stenotic plaque, which is sometimes referred to as thrombosis-resistant plaque, can generally be treated effectively by the known intravascular lumen opening techniques mentioned above. Although the stenosis they induce may benefit from treatment, these atherosclerotic plaques themselves are often a benign and effectively treatable disease.

Unfortunately, as plaque matures, narrowing of a blood vessel by a proliferation of smooth muscle cells, matrix synthesis, and lipid accumulation may result in formation of a plaque which is quite different than a standard stenotic plaque. Such atherosclerotic plaque often becomes thrombosis-prone, and can be highly dangerous. This thrombosis-prone or vulnerable plaque may be a frequent cause of acute coronary syndromes.

The characterization of these vulnerable (and potentially life-threatening) plaques is currently under investigation. A number of strategies have been proposed to detect a vulnerable plaque. Proposed strategies include angiography, intravascular ultrasound, angioscopy, magnetic resonance imaging, magnetic resonance diffusion imaging, spectroscopy, infrared spectroscopy, scintigraphy, optical coherence tomography, electron beam computed tomographic scanning, and thermography, all of which have had limited success. In particular, proposed thermography methods detect temperature variations, as vulnerable plaque is typically inflamed and as such gives off more heat than standard stenotic plaque. While current thermography methods show promise, they continue to suffer from limited temperature sensitivity which may often result in inaccurate detections of vulnerable plaque.

While the known procedures for treating plaque have gained wide acceptance and shown good efficacy for treatment of standard stenotic plaques, they may be ineffective (and possibly dangerous) when thrombotic conditions are superimposed on atherosclerotic plaques. Specifically, mechanical stresses caused by primary treatments like PTA or stenting may actually trigger release of fluids and/or solids from a vulnerable plaque into the blood stream, thereby potentially causing a coronary thrombotic occlusion.

For these reasons, it would be desirable to provide methods, apparatus, and kits for the detection and treatment of vulnerable plaque in blood vessels. The methods and apparatus should be suitable for intravascular and intraluminal introduction, preferably via a percutaneous approach. It would be particularly desirable if the new methods and apparatus were able to detect the vulnerable plaque accurately and/or deliver the treatment in a very controlled and safe manner, with minimal deleterious effects on adjacent tissues. Treatment methods, apparatus, and kits should further be effective in inhibiting release of the vulnerable plaque with minimum side effects. At least some of these objectives will be met by the invention described herein.

2. Description of the Background Art

A cryoplasty device and method are described in PCT Publication No. WO 98/38934. Balloon catheters for intravascular cooling or heating a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901,241. Catheters with heated balloons for postangioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336,691. The following U.S. Patents may also be relevant to the present invention: U.S. Pat. Nos. 5,458,612; 5,545,195; and 5,733,280.

Thermography is described by Ward Casscells, et al. in *The Vulnerable Atherosclerotic Plaque: Understanding, Identification, and Modification*, Chpt. 13, pp. 231–242 (1999); and in L. Diamantopoulos, et al. at the following Internet address: http://www.eurekalert.org/releases/ahaati041499.html. The impact of low temperatures on lipid membranes is described by Jack Kruuv in an article entitled *Advances in Molecular and Cell biology*, vol. 19, pp. 143–192 (1997); P. J. Quinn in *Cryobiology*, Vol. 22, pp. 128–146 (1985); and Michael J. Taylor, Ph.D. in *Biology Of Cell Survival In The Cold*, (Harwood Academic Publishers, In Press).

The full disclosures of each of the above references are incorporated herein by reference.

SUMMARY OF THE INVENTION

The present invention provides detection and treatment of vulnerable plaque within a blood vessel of a patient. The blood vessel may be any blood vessel in the patient's vasculature, including veins, arteries, and particularly coronary arteries. The vessel will typically be partially stenosed, at least in part from vulnerable plaque. In particular, the present invention may inhibit release of retained fluid within the vulnerable plaque so as to inhibit acute coronary syndrome and to help maintain the patency of a body lumen. The present invention may also provide for the treatment of vulnerable plaque in carotid arteries for stroke prevention. Where the patient's vasculature has both the vulnerable plaque and standard stenotic plaque, the treatment techniques described herein may be selectively directed to the vulnerable plaque, optionally without substantial cooling of the standard stenotic plaque. In other embodiments, both types of plaque may be treated.

In a first aspect, the present invention provides a method for treating vulnerable plaque of a blood vessel. The method comprises cooling the vulnerable plaque to a temperature sufficient to inhibit release of retained fluid from within the vulnerable plaque into the blood stream. The cooling treatment will often be directed against all or a portion of a circumferential surface of a lumen of the blood vessel, and will preferably inhibit release of lipid-rich liquid being releasably retained by the vulnerable plaque.

Optionally, a portion of the vasculature may be identified in which releasing of the retained fluid should be inhibited. For example, releasing of the retained fluid from a vulnerable plaque in some cardiac arteries may result in sudden cardiac death. Releasing of the retained fluid from a vulnerable plaque in the carotid arteries may result in stroke. Hence, when it is determined that a plaque is located within such a portion of the vasculature, the cooling step may be performed at this identified plaque location. Optionally, such cooling may be performed without specifically identifying the plaque as a vulnerable plaque. In other embodiments, the vulnerable plaque may be differentiated from standard stenotic plaque, often prior to initiation of the cooling. Hence, the cooling may be selectively directed at vulnerable plaque, rather than being applied to plaque in general. Advantageously, a single balloon catheter may be used to both differentiate and treat the vulnerable plaque.

Differentiation of vulnerable plaque from standard stenotic plaque may be enhanced by the use of a balloon catheter inflated with a gas. The differentiation may be effected using a temperature sensor for sensing a temperature of a tissue adjacent the balloon. Surprisingly, plaque differentiation benefits from gas temperatures within the balloon of about 20° C. or more, preferably being 30° C. or more. Hence, the balloon may be inflated so that an initial temperature of the gas within the balloon is about 30° C. Inflation with such a warm gas can amplify the measured temperature differences (for example) sensed by temperature sensors distributed along a balloon wall and in thermal engagement with the vulnerable plaque (at a first sensor) and a standard stenotic plaque or healthy luminal wall (at a second sensor).

Cooling of the vessel may be effected by introducing a catheter into a lumen of the blood vessel. A first balloon is positioned within the vessel lumen adjacent the vulnerable plaque. Cryogenic cooling fluid is introduced into the first balloon and exhausted. A second balloon disposed over the first balloon is expanded to radially engage the vessel lumen. Generally, the temperature of an inside surface of the first balloon will be in the range from about −55° C. to −75° C. and an outside surface of the first balloon will be in the range from about −25° C. to −45° C. The temperature of an outside surface of the second balloon will be in the range from about 10° C. to −40° C., preferably from about 10° C. to −20° C., more preferably from about 5° C. to −10° C. In alternative embodiments, the temperature of an inside surface of the first balloon may be in a range from about −30 C to −50 C, and an outside surface of the first balloon may be in a range from about −20 C to −40 C.

Usually, the temperature at the surface of the blood vessel lumen is in the range from about 10° C. to −40° C., preferably from about 10° C. to −20° C., more preferably from about 5° C. to −10° C. The tissue is typically maintained at the desired temperature for a time period in the range from about 15 seconds to 120 seconds, preferably from 30 seconds to 60 seconds, optionally being in a range from about 20 seconds to about 60 seconds. Vulnerable plaque stabilization may be enhanced by repeating cooling in cycles, typically with from about 1 to 3 cycles, with the cycles being repeated at a rate of about one cycle every 120 seconds.

Surprisingly, cooling temperatures above 0° C. can effect a transition of the vulnerable plaque's lipid core from a disordered cystalline state fluid to a ordered crystalline state solid or gel. Thus, vulnerable plaque can be stabilized by cooling the lipid-rich liquid sufficiently to change a state of the lipid-rich liquid, typically to a highly ordered hexagonal lattice at transition temperatures generally in the range from about 10° C. to −10° C. The stabilization may, at least in part, remain in effect after subsequent return of the tissue to a normal body temperature. The stabilization may, at least in part, be transitory, with the stabilization effect diminishing and/or disappearing after cooling is terminated. The vulnerable plaque may be treated while it remains at least partially stabilized.

Advantageously, the cooling may be accurately controlled to tailor a desired tissue response. Cooling may be performed so as to cause apoptosis and/or necrosis in the tissues comprising or adjacent to the vulnerable plaque. Alternatively, the cooling may also be performed in a manner that avoids causing apoptosis and/or necrosis. Cooling may stabilize the vulnerable plaque while inhibiting necrosis and/or apoptosis of tissue adjacent the lipid-rich liquid, particularly of the tissues defining a cap of cells between the lipid-rich liquid and the lumen of the blood vessel. Cooling may also inhibit inflammation and deterioration of the vulnerable plaque. The cooling treatment may further inhibit rupture of the cap of cells of the vulnerable plaque.

In other aspects, the present invention of cooling the vulnerable plaque to inhibit release of lipid-rich liquid may be combined with additional treatments. For example, one adjunctive method may comprise treating the cooled vulnerable plaque with a primary treatment. Suitable primary treatments may include balloon angioplasty, atherectomy, rotational atherectomy, laser angioplasty, or the like, where the lumen of the treated blood vessel is enlarged to at least partially alleviate a stenotic condition. The primary treatment may also include procedures for controlling restenosis, such as stent placement. In the case of arteries, the primary treatment will be effected shortly before, during, or preferably very shortly after the cooling treatment, preferably within 60 seconds of the cooling treatment, more preferably immediately following the cooling of the lipid-rich liquid to a desired temperature. Alternatively, cooling methods may additionally comprise passivating the vulnerable plaque by reducing a size of the lipid-rich liquid, changing a cellular consistency or composition of the lipid-rich liquid, enhancing a structural integrity of the cap (e.g. increasing a thickness of the cap), modifying a cellular composition or structural properties of the cap, and/or the like by altering the chemistry or life cycle of the vulnerable plaque.

In another aspect, the present invention provides a method for treating vulnerable plaque of a blood vessel, the vulnerable plaque releasably retaining fluid. The method includes detecting the vulnerable plaque with a balloon catheter and cooling the vulnerable plaque with the balloon catheter to a temperature sufficient to inhibit release of the retained fluid into the blood vessel.

Preferably, the detecting step will comprise inflating a balloon of the balloon catheter so that a gas within the balloon is at a temperature of 30° C. or more. The cooling step may comprise cooling an outer surface of the balloon to a temperature of about 10° C. or less.

In another aspect, the present invention provides a method for detecting vulnerable plaque of a blood vessel. The method includes positioning a balloon within the vessel lumen adjacent a plaque. The balloon is inflated so that a plurality of temperature sensors affixed to the balloon are coupled to a surface of the vessel lumen. A temperature differential along the lumen surface is sensed with the sensors.

The inflating step may be performed so that the gas within the balloon has a temperature of about 20° C. or more, the balloon preferably being inflated so that the gas has an initial temperature in the balloon of 30° C. or more. Surprisingly, temperature sensors along the balloon wall can detect a temperature differential of greater than about 1° C. between a vulnerable plaque and an adjacent portion of the luminal wall with such a system. Additionally, the size of the "hot" region disposed along the vessel wall may increase when the balloon is inflated with the gas. Hence, the use of a warm gas within a balloon catheter can act to amplify the sensitivity of the system for detection of vulnerable plaques.

In another aspect, the present invention provides a cryotherapy catheter for detecting and treating vulnerable plaque of a blood vessel having a lumen surface. The catheter generally comprises a catheter body having a proximal end and a distal end with a cooling fluid supply lumen and an exhaust lumen extending therebetween. A first balloon is disposed near the distal end of the catheter body in fluid communication with the supply lumen and exhaust lumen. A second balloon is disposed over the first balloon with a thermal barrier therebetween. A plurality of temperature sensors are affixed to the second balloon so as to provide temperature measurements of the lumen surface.

In another aspect, the present invention provides a catheter for detecting a vulnerable plaque of a blood vessel having a lumen surface. The catheter generally comprises a catheter body having a proximal end and a distal end with a supply lumen and an exhaust lumen extending therebetween. A balloon is disposed on the distal end of the catheter body in fluid communication with the supply lumen and exhaust lumen. A plurality of temperature sensors are supported by the balloon so as to provide temperature measurements of the lumen surface.

Optionally, an inflation supply may be in fluid communication with the supply lumen at the proximal end of the catheter body. The inflation supply may be configured to inflate the balloon with a gas when detecting the vulnerable plaque. The gas in the balloon may have a temperature of about 20° C. or more during the temperature measurements. In some embodiments, the inflation supply may further be configured to direct cooling fluid to the balloon in a treatment mode so that an outer temperature of the balloon is about 10° C. or less.

In another aspect, the invention also provides a kit for treating vulnerable plaque in a blood vessel. The kit comprises a catheter having a proximal end, a distal end, and a cooling member near its distal end. Instructions are included in the kit for use of the catheter. These instructions comprise the step of cooling the blood vessel adjacent the vulnerable plaque to inhibit release of the retained fluid into the blood vessel. Such a kit may include instructions for any of the methods described herein.

In yet another aspect, the invention provides a kit for detecting vulnerable plaque of a blood vessel. The kit comprises a catheter having a proximal end, a distal end, and a balloon member with a plurality of temperature sensors near its distal end. Instructions are included in the kit for use of the catheter. These instructions comprise the steps of positioning a balloon within the vessel lumen adjacent a plaque, inflating the balloon so that a plurality of temperature sensors affixed to the balloon are coupled to a surface of the vessel lumen, and sensing a temperature differential along the lumen surface with the sensors. Such a kit may include instructions for any of the methods described herein.

BRIEF DESCRIPTION OF THE DRAWINGS

FIG. 5 illustrates an exemplary cryotherapy catheter for detecting and treating vulnerable plaque.

FIG. 6 is a cross-sectional view of the catheter taken along line 6—6 in FIG. 5.

FIG. 10A illustrates an alternative catheter for detecting vulnerable plaque.

FIG. 10B is a cross-sectional view of the catheter taken along line 10B—10B in FIG. 10A.

DESCRIPTION OF THE SPECIFIC EMBODIMENTS

Figure 1A:
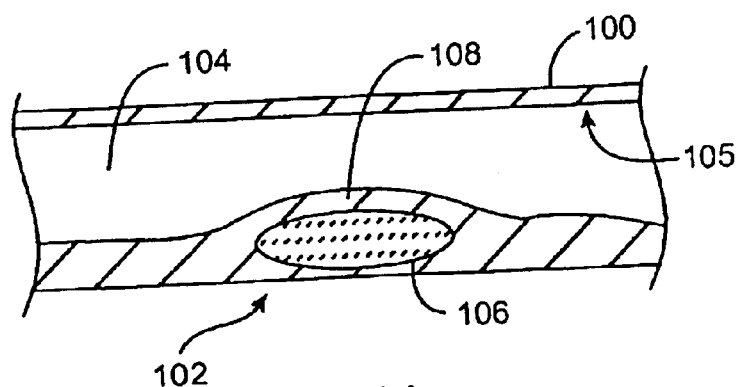
FIGS. 1A and 1B are cross-sectional views of a blood vessel containing a mature vulnerable plaque.
Figure 1B:
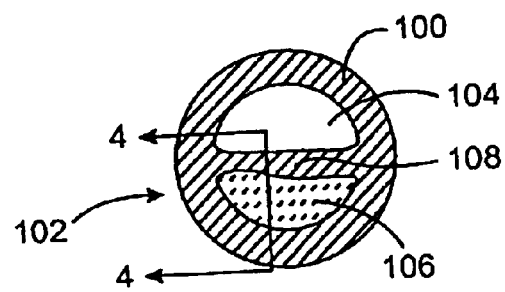
Figure 2:
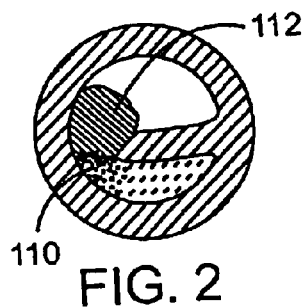
FIG. 2 illustrates a cross-sectional view of a vulnerable plaque rupture and plaque hemorrhage in the blood vessel.
Figure 3:
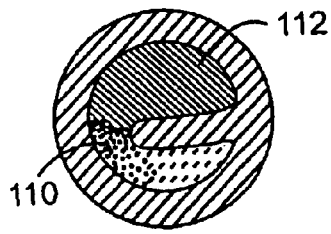
FIG. 3 illustrates a cross-sectional view of a thrombotic occlusion in the blood vessel.

As used herein, the terms "vulnerable plaque" and "hot plaque" refer to atherosclerotic plaque that is thrombosis-prone. FIGS. 1A and 1B illustrate cross-sectional views of a blood vessel 100 containing a mature vulnerable plaque 102 within a lumen 104 of the vessel. The vulnerable plaque 102 generally comprises a necrotic core 106 of soft, lipid-rich, atheromatous gruel and a fibrous, sclerotic cap 108 of a collagen matrix of smooth muscle cells that covers the core 106. The gruel generally comprises a liquid of esterified cholesterol and low density lipoproteins which is releasably retained by the vulnerable plaque 102. Disruption or fissuring of the cap 108 may cause plaque hemorrhage 110 (release of the highly thrombogenic lipid-rich liquid 106 through the ruptured plaque), as seen in FIG. 2. As a result of plaque hemorrhage 110, the highly thrombogenic lipid-rich liquid 106 is exposed to flowing blood of the vessel lumen 104. As illustrated in FIG. 3, release of the thrombogenic liquid may cause a thrombotic occlusion 112 (blood clot) of the entire vessel lumen, which in turn may be lead to life-threatening conditions, such as a stroke or sudden cardiac death.

Figure 4:
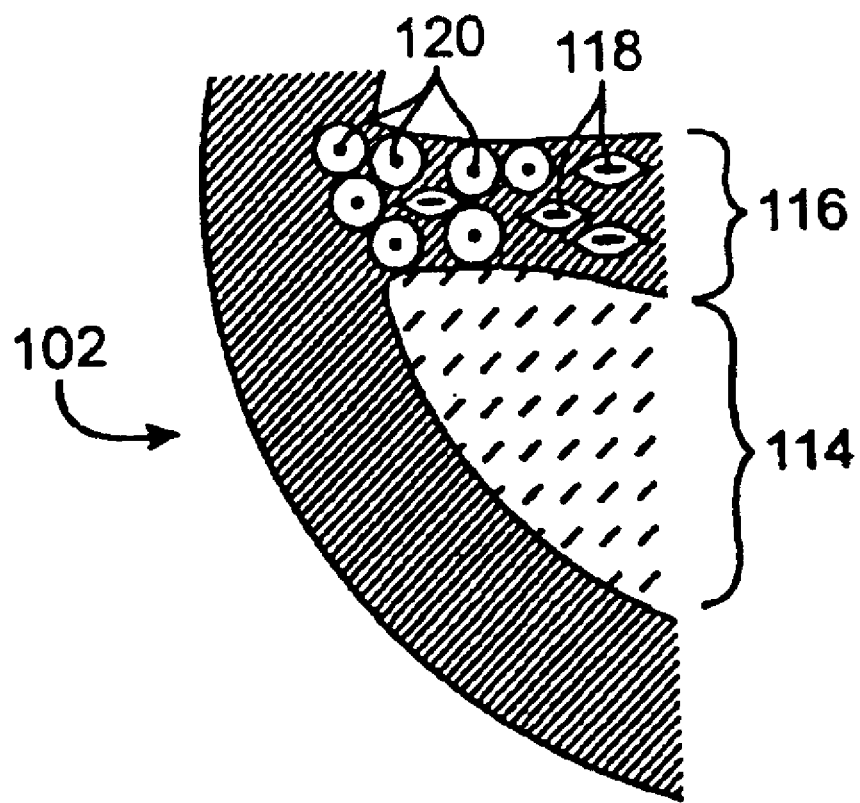
FIG. 4 illustrates an exploded cross-sectional view of FIG. 1A taken along line 4—4.

Three determinants of vulnerability are illustrated in FIG. 4, which is an exploded cross-sectional view of FIG. 1B taken along line 4—4. Susceptibility of a vulnerable plaque to rupture may be primarily determined from the size 114 and consistency of the athermanous core (e.g. a larger core increases chances for rupture), the thickness 116 and structural integrity of the sclerotic cap (e.g. a thinner cap increases chances for rupture), and cap inflammation (e.g. macrophage foam cell 118 infiltration weakens the cap 120 and increases chances for rupture). Additionally, vulnerable plaque disruption may be triggered by numerous extrinsic stresses imposed on the plaque. For example, fluctuations in intraluminal blood pressure, pulse pressure, heart contraction, vasospasm, and the like may precipitate disruption of a vulnerable plaque. Alternatively, mechanical stresses caused by primary treatments like PTA or stenting may trigger rupture as well.

Referring now to FIGS. 5 and 6, an exemplary cryotherapy catheter 10 (which is more fully described in co-pending application Ser. No. 09/619,583 filed Jul. 19, 2000 the full disclosure of which is incorporated herein by reference) for detecting and treating vulnerable plaque 102 of a blood vessel 100 having a lumen surface 105 (see FIG. 1A) will be described. The catheter 10 comprises a catheter body 12 having a proximal end 14 and a distal end 16 with a cooling fluid supply lumen 18 and an exhaust lumen 20 extending therebetween. A first balloon 22 is disposed near the distal end of the catheter body 12 in fluid communication with the supply and exhaust lumens. A second balloon 24 is disposed over the first balloon 22 with a thermal barrier 26 therebetween.

The balloons 22, 24 may be an integral extension of the catheter body 12, but such a structure is not required by the present invention. The balloons 22, 24 could be formed from the same or a different material as the catheter body 12 and, in the latter case, attached to the distal end 16 of the catheter body 12 by suitable adhesives, heat welding, or the like. The catheter body 12 may be formed from conventional materials, such as polyethylenes, pebax, polyimides, and copolymers and derivatives thereof. The balloons 22, 24 may also be formed from conventional materials used for angioplasty, preferably being inelastic, such as polyethylene terephthalate (PET), polyethylene, pebax, or other medical grade material suitable for constructing a strong non-distensible balloon. Additionally, balloons 22 and 24 could be formed from different material to provide improved protection. For example, the first balloon 22 could be formed from PET to provide strength while the second balloon 24 could be formed from polyethylene to provide durability. The balloons 22, 24 have a length of at least 1 cm each, more preferably in the range from 2 cm to 5 cm each. The balloons 22, 24 will have diameters in the range from 2 mm to 5 mm each in a coronary artery and 2 mm to 10 mm each in a peripheral artery.

The thermal barrier 26 may comprise a gap maintained between the balloons 22, 24 by a filament. The filament typically comprises a helically wound, braided, woven, or knotted monofilament. The monofilament may be formed from PET or polyethylene napthlate (PEN), and affixed to the first balloon 22 by adhesion bonding, heat welding, fasteners, or the like. The thermal barrier 26 may also comprise a gap maintained between the balloons 22, 24 by a plurality of bumps on an outer surface of the first balloon 22 and/or an inner surface of the second balloon 24. The plurality of bumps may be formed in a variety of ways. For example, the bumps may be intrinsic to the balloon (created during balloon blowing), or the bumps could be created by deforming the material of the balloon wall, by affixing mechanical "dots" to the balloon using adhesion bonding, heat welding, fasteners, or the like. Alternatively, the thermal barrier 26 may comprise a gap maintained between the balloons 22, 24 by a sleeve. The sleeve may be perforated and formed from PET or rubbers such as silicone and polyurathane. Still further structures might be employed to maintain a gap between the balloons, including a liquid.

Hubs 34 and 36 are secured to the proximal end 14 of the catheter body 12. Hub 34 provides a port 38 for connecting a cryogenic fluid source to the fluid supply lumen 18 which is in turn in fluid communication with the inner surface of the first balloon 22. Hub 34 further provides a port 40 for exhausting the cryogenic fluid which travels from balloon 22 in a proximal direction through the exhaust lumen 20. Hub 36 provides a port 42 for a guidewire which extends through a guidewire lumen 44 in the catheter body 12. Typically, the guidewire lumen 44 will extend through the exhaust lumen 20, as shown in FIG. 6. The guidewire lumen 44 may also extend axially outside the exhaust lumen 20 to minimize the occurrence of cryogenic fluid entering the blood stream via the guidewire lumen 44. Optionally, the guidewire lumen 44 may extend outside the inner surface of the first balloon 22 or the guidewire lumen 44 may allow for a guidewire to extend outside both balloons 22, 24. Additionally, a reinforcing coil 46 may extend along the catheter body 12 proximal the first balloon 22. The reinforcing coil 46 may comprise a simple spring having a length typically in the range from 6 cm to 10 cm to prevent the catheter 10 from kinking up inside the blood vessel.

The cryotherapy catheter 10 in FIG. 5 additionally illustrates a safety mechanism that monitors the containment of the first and second balloons 22, 24. The first balloon 22 defines a volume in fluid communication with the supply and exhaust lumens. A fluid shutoff is coupled to a cryogenic fluid supply with the supply lumen 18. The second balloon 24 is disposed over the first balloon 22 with a vacuum space 52 therebetween. The vacuum space 52 is coupled to the fluid shutoff so as to inhibit flow of cryogenic fluid into the first balloon 22 in response to a change in the vacuum space 52.

Figure 7:
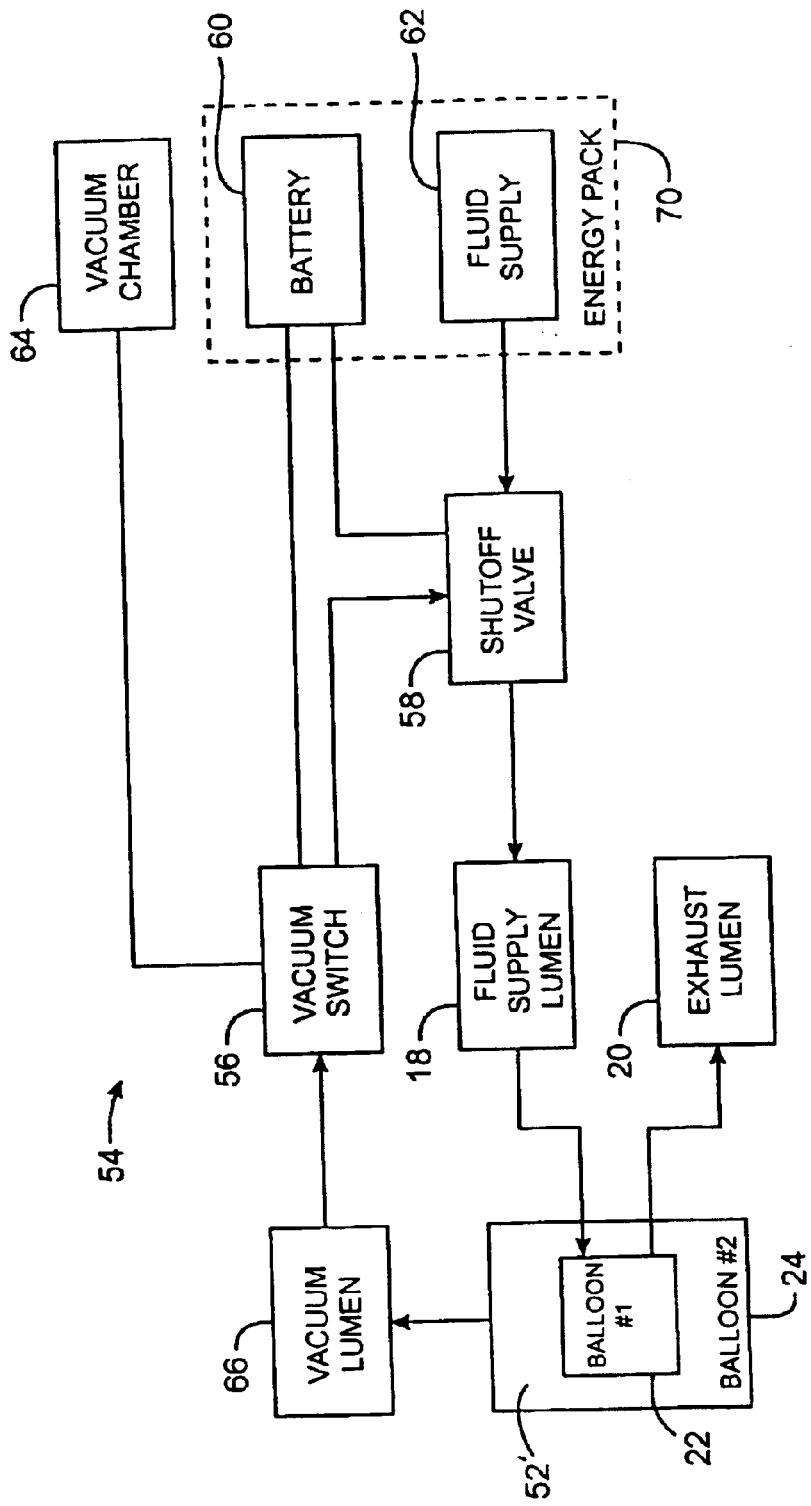
FIG. 7 is a functional flow diagram illustrating the operation of an automatic fluid shutoff mechanism of the catheter of FIG. 5.

FIG. 7 illustrates a functional flow diagram of the automatic fluid shutoff mechanism 54. The fluid shutoff 54 typically comprises a vacuum switch 56 connected to a shutoff valve 58 by a circuit, the circuit being powered by a battery 60. The switch 56 may remain closed only when a predetermined level of vacuum space 52 is detected in the second balloon 24. The closed switch 56 allows the shutoff valve 58, in fluid communication with the cryogenic fluid supply 62, to be open. Alternatively, the circuit may be arranged so that the switch 56 is open only when the predetermined vacuum space 52 is present, with the shutoff valve 58 being open when the switch is open. The vacuum space 52 is reduced when either the first balloon 22 is punctured, allowing cryogenic fluid to enter the vacuum space 52, or the second balloon 24 is punctured, allowing blood to enter the vacuum space 52. In addition to monitoring the containment of both balloons 22, 24, in the event of a failure, the vacuum switch 56 will be triggered to prevent the delivery of additional cryogenic fluid from the fluid supply 62 into the supply lumen 18. The second balloon 24 also acts to contain any cryogenic fluid that may have escaped the first balloon 22.

Figure 8A:
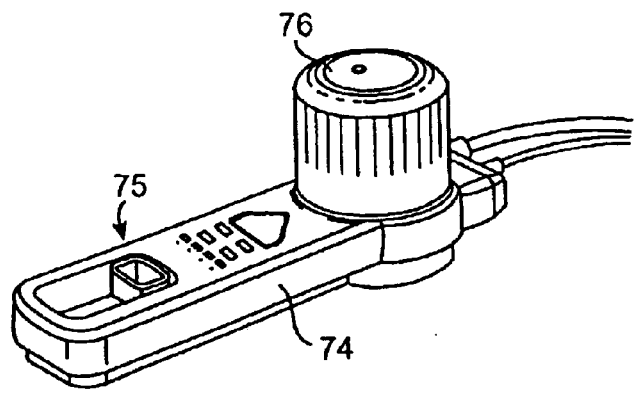
FIGS. 8A and 8B illustrate a handle and removable energy pack for use in the cryotherapy catheter of FIG. 5.
Figure 8B:
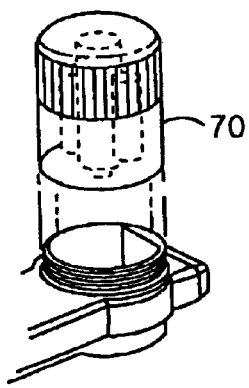

The vacuum space 52 may be provided by a simple fixed vacuum chamber 64 coupled to the vacuum space 52 by a vacuum lumen 66 of the body 12 via a vacuum port 68 (See FIG. 5). In the exemplary embodiment, a positive displacement pump (ideally being similar to a syringe) is disposed within handle 74 and may be actuated by actuator 75, as seen in FIG. 8A. The vacuum space 52 should comprise a small volume of vacuum in the range from 1 mL to 100 mL, preferably 10 mL or less, as a smaller vacuum space 52 facilitates detection of a change in the amount of vacuum when a small amount of fluid leakage occurs. The cryogenic fluid supply 62 and battery 60 for powering the circuit may be packaged together in an energy pack 70, as seen in FIG. 8B. The energy pack 70 is detachable from a proximal handle 74 of the catheter body and disposable. A plurality of separate replaceable energy packs 70 allow for multiple cryogenic cooling cycles. Alternative fluid supply and battery structures might also be employed, including those described in U.S. patent application Ser. No. 09/953464, filed on Sep. 14, 2001 and assigned to the assignee of the present application, the full disclosure of which is incorporated herein by reference.

An audio alert or buzzer 76 may be located on the handle 74, with the buzzer providing an audio warning unless the handle is maintained sufficiently upright to allow flow from the fluid supply 62. The cryotherapy catheter may additionally comprise a hypsometer 72 coupled to the volume by a thermistor, thermocouple, or the like located in the first balloon 22 or handle to determine the pressure and/or temperature of fluid in the first balloon 22. The hypsometer allows for accurate real time measurements of variables (pressure, temperature) that effect the efficacy and safety of cryotherapy treatments.

Figure 9:
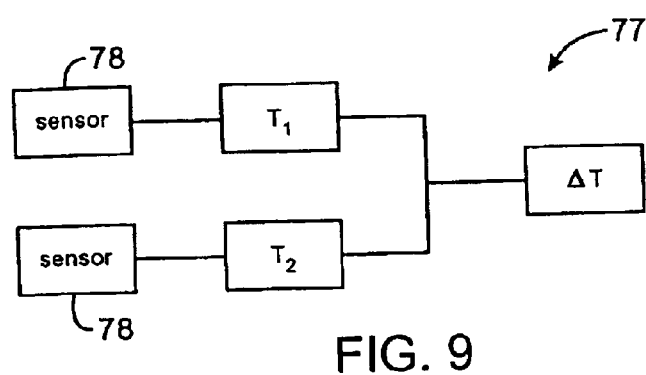
FIG. 9 illustrates a block diagram of a circuit which measures a temperature differential of the lumen surface.

The dual balloon cryotherapy catheter 10 in FIG. 5 also illustrates a temperature sensing mechanism that provides for thermographic detection of vulnerable plaque. A plurality of temperature sensors 78 are affixed to the second balloon 24 so as to provide direct temperature measurements of the lumen surface 105 (see FIG. 1A). The temperature sensors 78 may comprise a plurality of up to 20 thermocouples or thermistors and may be capable of detecting temperature differences greater than 0.1° C. Alternative temperature sensors might also be employed including a fiber optic cable connected to an infrared detector, resistance temperature detectors, or the like. The temperature sensors 78 may be secured to the second balloon 24 at a series of axial and circumferential locations. The plurality of temperature sensors 78 may be affixed by adhesion bonding, heat welding, fasteners, or the like to an outer surface of the second balloon 24, as shown in FIG. 5, or may be alternatively affixed to an inner surface of the second balloon 24. Still further alternatives are also possible, including attaching the sensors to, impregnating the sensors in, and/or forming the sensors on an insulation layer or other material disposed between the balloons. Temperature sensor wires 80 may be secured along the length of the catheter shaft 12 within a thin sleeve 82 formed from PET or rubbers such as silicone and polyurathane, or in the latter case the wires 80 may be threaded through the vacuum lumen 66. A connector 84 at the proximal end 14 of the catheter 10 may also be provided to connect the temperature sensor wires 80 to a temperature readout device for temperature mapping along the lumen surface. Additionally, a circuit 77 may be attached to the connector 84 for measuring a temperature differential ΔT along the lumen surface from temperature measurement T1 and T2 sensed by the temperature sensors 78, as illustrated in the block diagram of FIG. 9. An indicator which is triggered above a threshold temperature differential may also be located on the connector. An indicator signal indicating a temperature above a threshold temperature differential may optionally be used as a trigger to initiate treatment of the vulnerable plaque, with or without further input from the physician. Hence, the system may first diagnose a plaque as a hot plaque, optionally by inflating the balloon with a warm gas, and then automatically treat that hot plaque by inflating the balloon so as to (usually cryogenically) cool the hot plaque.

Detection of vulnerable plaque may be carried out by introducing the cryotherapy catheter 10 into a lumen 104 of the blood vessel 100 over a guidewire. The first balloon 22 is positioned within the blood vessel lumen 104 adjacent a plaque. The first balloon 22 is inflated so that the plurality of temperature sensors 78 affixed to the second balloon 24 (which expands upon inflation) thermally couple a surface of the vessel lumen. A temperature differential along the lumen surface 105 is sensed with the sensors. Inflation of balloon 22 may be effected by a gas, such as carbon dioxide, nitrous oxide, or the like, at a pressure in the range from about 5 psi to 50 psi. As used herein, "psi" encompasses pounds per square inch above ambient pressure, sometimes refered to as "psig." The balloon 22 will typically be inflated for a time period in the range from 10 to 120 seconds. The balloon catheter may sense for a temperature differential in a static position or as it moving along the lumen surface. Advantageously, temperature sensors 78 thermally engage the lumen surface to allow for direct temperature measurements to be made at specific locations along the lumen surface. This increased temperature sensitivity may in turn lead to improved temperature mapping and accurate vulnerable plaque detections. Cryotherapy catheter 10 may then be used for treating the detected vulnerable plaque as described in more detail below with reference to FIGS. 11A–11C.

An alternative catheter 10' for detecting a vulnerable plaque of a blood vessel having a lumen surface is illustrated in FIGS. 10A and 10B. Detection catheter 10' comprises a catheter body 12 having a proximal end 14 and a distal end 16 with a supply lumen 88 and an exhaust lumen 88 extending therebetween. A balloon 86 is disposed on the distal end of the catheter body 12. Balloon 86 has an inner surface in fluid communication with the supply lumen and exhaust lumen. A plurality of temperature sensors 78 are affixed to an outer surface of the balloon 86 so as to provide direct temperature measurements of the lumen surface 105 (see FIG. 1A).

Detection of vulnerable plaque may be carried out by introducing the detection catheter 10' into a lumen 104 of the blood vessel 100 over a guidewire. The balloon 86 is positioned within the vessel lumen adjacent a plaque. The balloon 86 is inflated so that a plurality of temperature sensors 78 affixed to the balloon thermally couple a surface of the vessel lumen. A temperature differential along the lumen surface is sensed with the sensors. Balloon 86 is generally inflatable with standard inflation media, such as contrast, saline, or the like. An inflation media supply and/or exhaust port 90 is connected to the supply and/or exhaust lumen 88 which is in turn in fluid communication with the inner surface of balloon 86. Balloon 86 will typically be inflated for a time period in the range from 10 to 120 seconds. The balloon catheter may sense for a temperature differential in a static position or as it moving along the lumen surface.

Figure 11A:
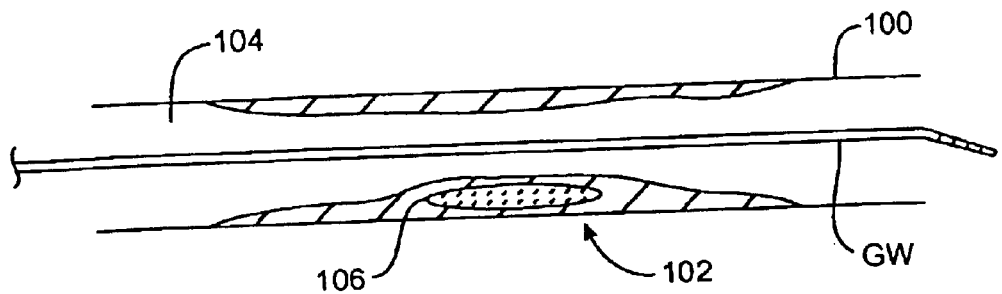
FIGS. 11A–11C illustrate use of the catheter of FIG. 5 for treatment of vulnerable plaque.
Figure 11B:
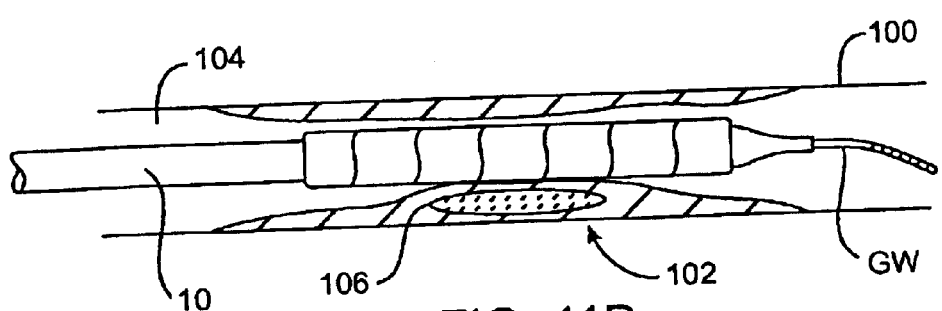
Figure 11C:
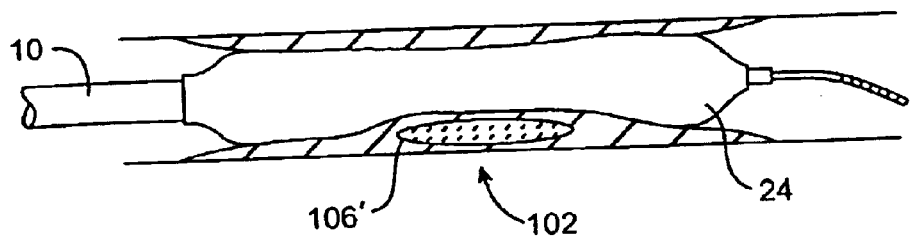

Referring now to FIGS. 11A through 11C, use of cryotherapy catheter 10 of FIG. 5 for treatment of vulnerable plaque 102 will be described. As illustrated in FIGS. 11A and 11B, catheter 10 will be introduced into a lumen 104 of the blood vessel 100 over a guidewire GW. The first balloon 22 is positioned within the blood vessel lumen 104 adjacent the vulnerable plaque 102. Cryogenic cooling fluid is introduced into the first balloon 22 (in which it often vaporizes) and exhausted. The second balloon 24 expands to radially engage the vessel wall, as illustrated by FIG. 11C. The vaporized fluid serves both to inflate balloon 22 (and expand balloon 24) and to cool the exterior surface of the balloons 22, 24. The blood vessel 100 adjacent the vulnerable plaque 102 is cooled to a temperature sufficient to inhibit release of retained fluid 106 from within the vulnerable plaque 102 into the blood vessel 100. The cooling treatment will be directed at all or a portion of a circumferential surface the vessel lumen. Preferably cooling will inhibit release of lipid-rich liquid being releasably retained by the vulnerable plaque by stabilizing the lipid-rich liquid 106 to a lipid-rich solid or gel 106' (which is described in more detail in FIGS. 12A–12B below). Heat transfer will also be inhibited between the first and second balloons 22, 24 by the thermal barrier 26 so as to limit cooling of the vulnerable plaque to a desired temperature profile. Additionally, containment of the first and second balloons 22, 24 will be monitored during cooling by the fluid shutoff mechanism (see FIG. 7).

Suitable cryogenic fluids will preferably be non-toxic and may include liquid nitrous oxide, liquid carbon dioxide, cooled saline and the like. The cryogenic fluid will flow through the supply lumen 18 as a liquid at an elevated pressure and will vaporize at a lower pressure within the first balloon 22. For nitrous oxide, a delivery pressure within the supply lumen 18 will typically be in the range from 600 psi to 1000 psi at a temperature below the associated boiling point. After vaporization, the nitrous oxide gas within the first balloon 22 near its center may have a pressure in the range from 15 psi to 100 psi, optionally having a pressure in a range from 50 to 150 psi. The nitrous oxide gas may have a pressure in the range from 50 psi to 100 psi in a peripheral artery, preferably having a pressure in a range from 100 to 150 in a peripheral artery, and may have a pressure in a range from about 15 psi to 45 psi in a coronary artery, preferably having a pressure in a range from 100 to 150 psi in a coronary artery.

The temperature of an inside surface of the first balloon may be in the range from about −55° C. to −75° C. (preferably being in a range from about −30 C to −50 C) and an outside surface of the first balloon may be in the range from about −25° C. to −45° C. (preferably being in a range from about −20 C to −40 C). The temperature of an outside surface of the second balloon will be in the range from about 10° C. to −40° C., preferably from about 10° C. to −20° C., more preferably from about 5° C. to −10° C. This will provide a desired treatment temperature in a range from about 10° C. to −40° C., preferably from about 10° C. to −20° C., more preferably from about 5° C. to −10° C. The tissue is typically maintained at the desired temperature for a time period in the range from about 15 to 120 seconds, optionally being from 30 to 60 seconds, preferably being from 20 to 60 seconds. Vulnerable plaque stabilization may be enhanced by repeating cooling in cycles, typically with from about 1 to 3 cycles, with the cycles being repeated at a rate of about one cycle every 120 seconds.

In some instances, cooling of the vessel may be limited to inhibit or avoid necrosis and/or apoptosis of tissue adjacent the lipid-rich liquid, particularly of the tissues defining a cap of cells 108 between the lipid-rich liquid 106 and the lumen of the blood vessel 104 (see FIG. 1A). Apoptosis or cell necrosis may be undesirable if it weakens the cap of cells as cap weakening may likely incite rupture of the vulnerable plaque and release of the lipid-rich liquid. Thus, the present invention may inhibit release of the retained fluid into the blood vessel without affecting the viability of the cap cells 108 and other cells which line the body lumen.

In other applications, cooling of the vessel at cooler temperatures may be desirable to provide for or induce apoptosis and/or programmed cell death stimulation of inflammatory cells (e.g. macrophages 118, see FIG. 4) in the vulnerable plaque 102. Apoptosis may be desirable as the presence of such inflammatory cells may trigger cap weakening or erosion which in turn may lead to vulnerable plaque release of the lipid-rich liquid. Cooling at temperatures in the range from about 0° C. to −15° C. may inhibit inflammation and deterioration of the vulnerable plaque, particularly of the tissues defining the cap of cells 108. Alternatively, it may be beneficial to provide for or induce necrosis in the cap cells 108 at cooling temperatures below about −20° C. Cap necrosis may stimulate cellular proliferation and thickening of the cap which in turn may inhibit cap rupture.

Figure 12A:
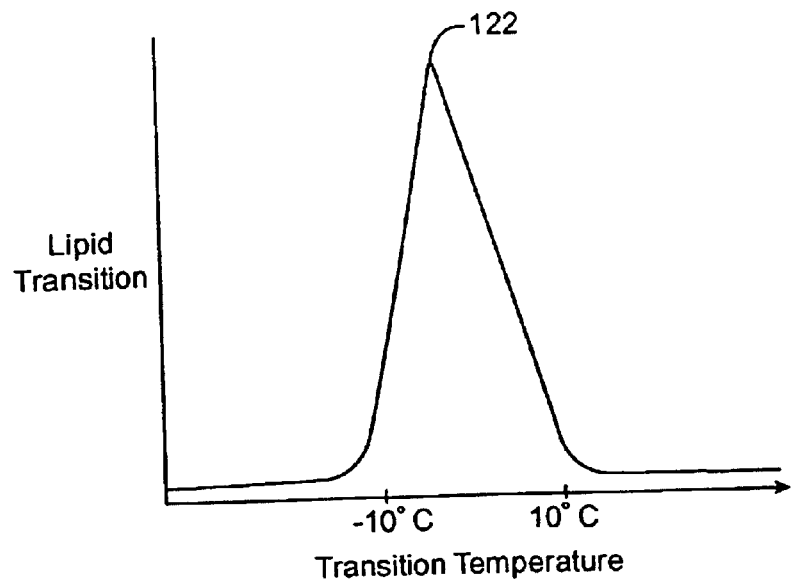
FIG. 12A is a graph illustrating a transition temperature which effects a lipid core transition of the vulnerable plaque.
Figure 12B:
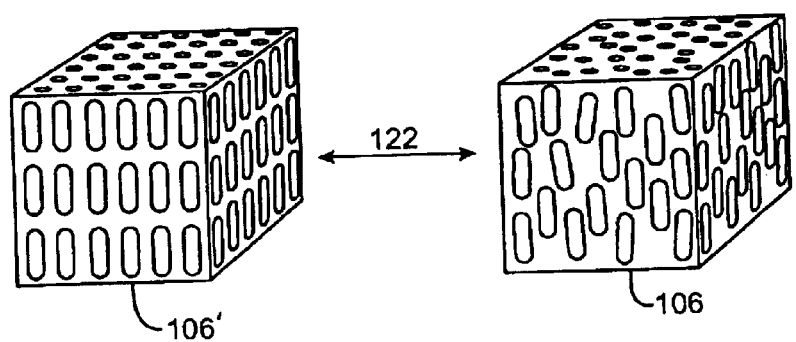
FIG. 12B illustrates the lipid core transition from a liquid, disordered state to a solid, ordered state.

Referring now to FIGS. 12A and 12B, transition of the vulnerable plaque's lipid-rich liquid core 106 will be described. FIG. 12A illustrates the transition temperature which effects a lipid core transition. The main transition point 122 occurs at some point between the transition temperature range of 10° C. to −10° C. At this transition point 122, the lipid core may undergo a phase change from a disordered crystalline state fluid 106 to a ordered crystalline state solid or gel 106', as shown in FIG. 12B. Thus, vulnerable plaque can be stabilized by cooling the lipid-rich liquid core 106 sufficiently to change its state, typically from a disordered lipid to a highly ordered hexagonal lattice. Advantageously, a transition temperature above −5° C. also inhibits necrosis and/or apoptosis of tissue adjacent the lipid-rich liquid 106, particularly of the cap 108.

Figure 13A:
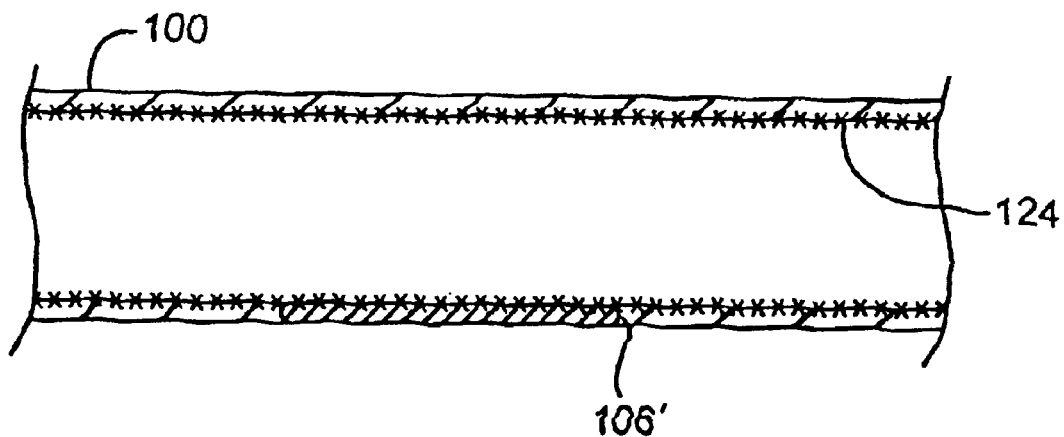
FIGS. 13A and 13B illustrate additional treatments in conjunction with cooling of the vulnerable plaque.
Figure 13B:
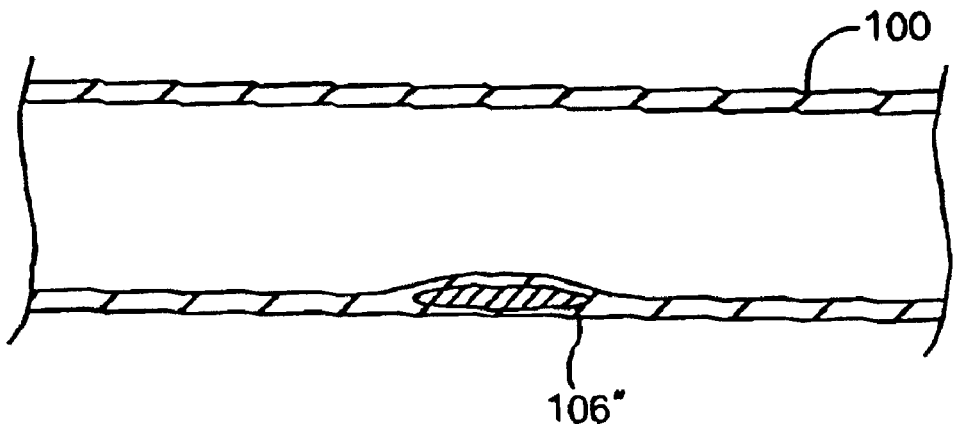

With reference now to FIGS. 13A and 13B, additional treatments in conjunction with cooling of the vulnerable plaque will be illustrated. FIG. 13A illustrates a cross section of a blood vessel 100 that has been cooled so that the vulnerable plaque has been stabilized to lipid-rich solid/gel 106'. A stent 124 has been placed within the vessel lumen while the plaque is stabilized to provide a long-term restraint of lipid-rich fluid 106, and possibly to provide a structural scaffolding for healthy endothelial cells via tissue ingrowth. The stent may also alleviate plaque-induced stenosis and to improve the patency of the lumen. Other suitable primary treatments of the stabilized plaque may include balloon angioplasty, atherectomy, rotational atherectomy, laser angioplasty, or the like, where the lumen of the treated blood vessel is enlarged to at least partially alleviate a stenotic condition. In the case of arteries, the primary treatment will be effected shortly before, during, or preferably very shortly after the cooling treatment, preferably within 60 seconds of the cooling treatment, more preferably immediately following the cooling of the lipid-rich liquid to a desired temperature. In some instances, cooling may effect passivation of the vulnerable plaque, possibly reducing a size of the lipid-rich liquid 106", as illustrated in FIG. 13B, or modifying a cellular consistency or composition of the lipid-rich liquid, and/or the like by altering the chemistry or life cycle of the vulnerable plaque. Passivation may also include enhancing a structural integrity of cap 108 (e.g. increasing the thickness, strength, elasticity, or hardness of the cap), modifying a cellular composition or property of the cap, and/or the like via scar formation or alteration of the chemistry of the vulnerable plaque.

Figure 14:
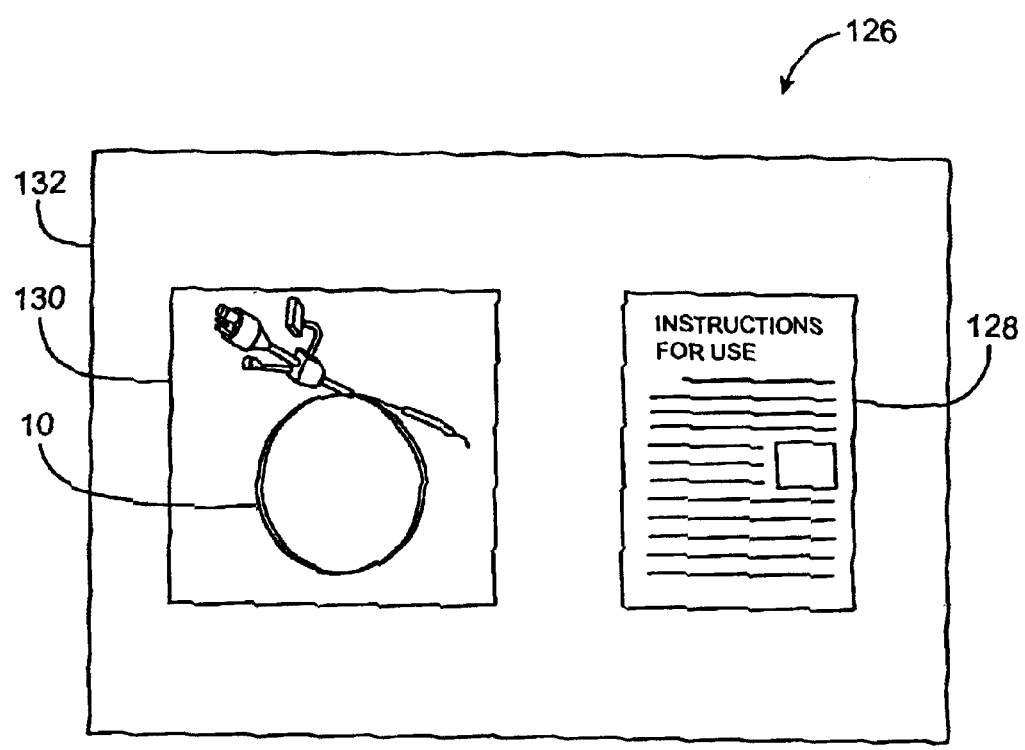
FIG. 14 illustrates a vulnerable plaque treatment kit including the apparatus of FIG. 5 and instructions for use.

A kit 126 including a catheter 10 and instructions for use 128 is illustrated in FIG. 14. Catheter 10 may comprise the dual balloon catheter of FIG. 5, as illustrated in FIG. 14, or a catheter having a proximal end, a distal end, and a cooling member near its distal end. Instructions for use 128 may describe any of the associated method steps set forth above for detection and/or treatment of vulnerable plaque. Instructions for use 128 will often be printed, optionally appearing at least in part on a sterile package 130 for balloon catheter 10. In alternative embodiments, instructions for use 128 may comprise a machine readable code, digital or analog data graphically illustrating or demonstrating the use of balloon catheter 10 to detect and/or treat vulnerable plaque. Still further alternatives are possible, including printing of the instructions for use on packaging 132 of kit 126, and the like.

Figure 15A:
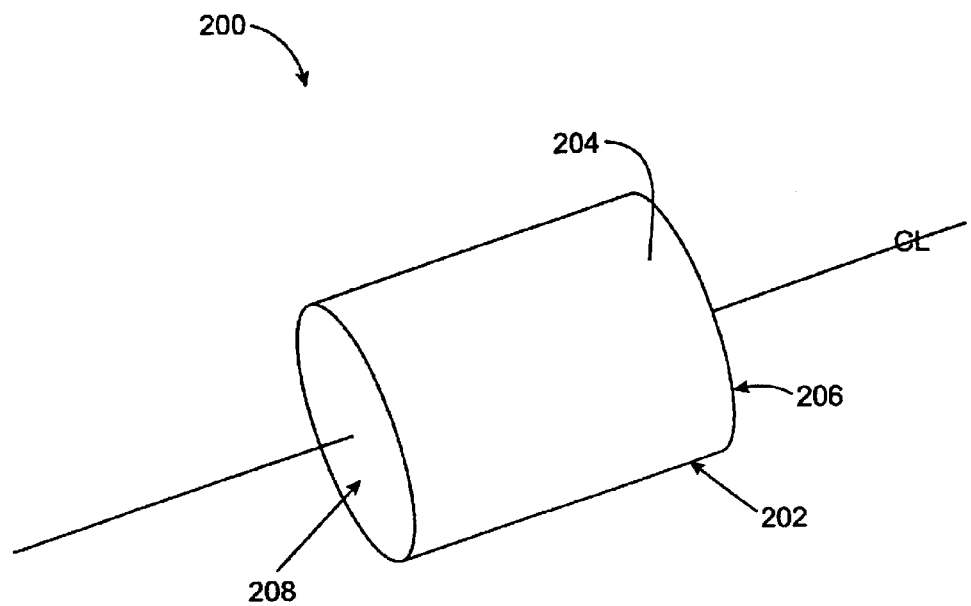
FIGS. 15A and 15B are a perspective view and a cross-sectional view, respectively of hot plaque thermal models.
Figure 15B:
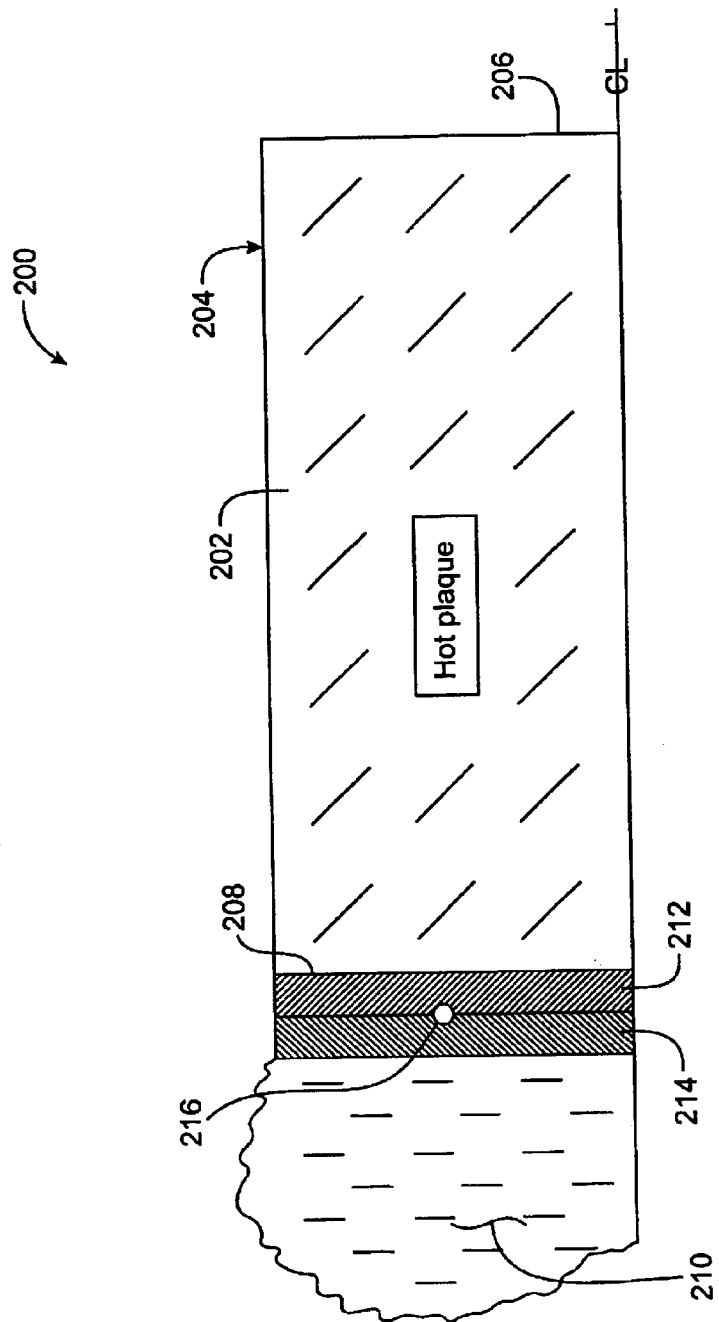

Referring now to FIGS. 15A and 15B, a thermal model 200 was developed to study heat transfer from a volume of hot plaque 202. Hot plaque 202 was assumed to be a cylinder having a diameter of 2 mm and a length of 2 mm. A circumferential surface 204 and a first end surface 206 of hot plaque 202 are thermally coupled to normal tissue at 37° C. A second end 208 of hot plaque 202 defines a portion of a luminal wall, and is thermally exposed directly to blood flow within the lumen of a blood vessel, or indirectly to a fluid within a balloon through a balloon wall (see FIG. 15B). Given the assumed cylindrical shape of hot plaque 202, the hot plaque (and its thermal characteristics) are radially symmetrical about a center line CL. Hence, the illustration shown in FIG. 15B (and subsequent graphs of temperature distribution within hot plaque 202) are illustrated as a radial cross-section beginning at the center line CL and ending at circumferential surface 204.

Heat transfer coefficients for thermal flows between hot plaque 202 and surrounding tissues can be modeled using known thermal properties of the tissue and/or by measuring the properties of appropriate human, animal or model tissues. Similarly, heat flow through luminal surface end 208 of hot plaque 202 may be based on known or measured heat transfer properties. The thermal model results described below make use of a heat transfer coefficient directly between a hot plaque surface 208 and a blood flow 210 within the lumen of 0.000594 W/mm$^2$–° C.

Figure 16A:
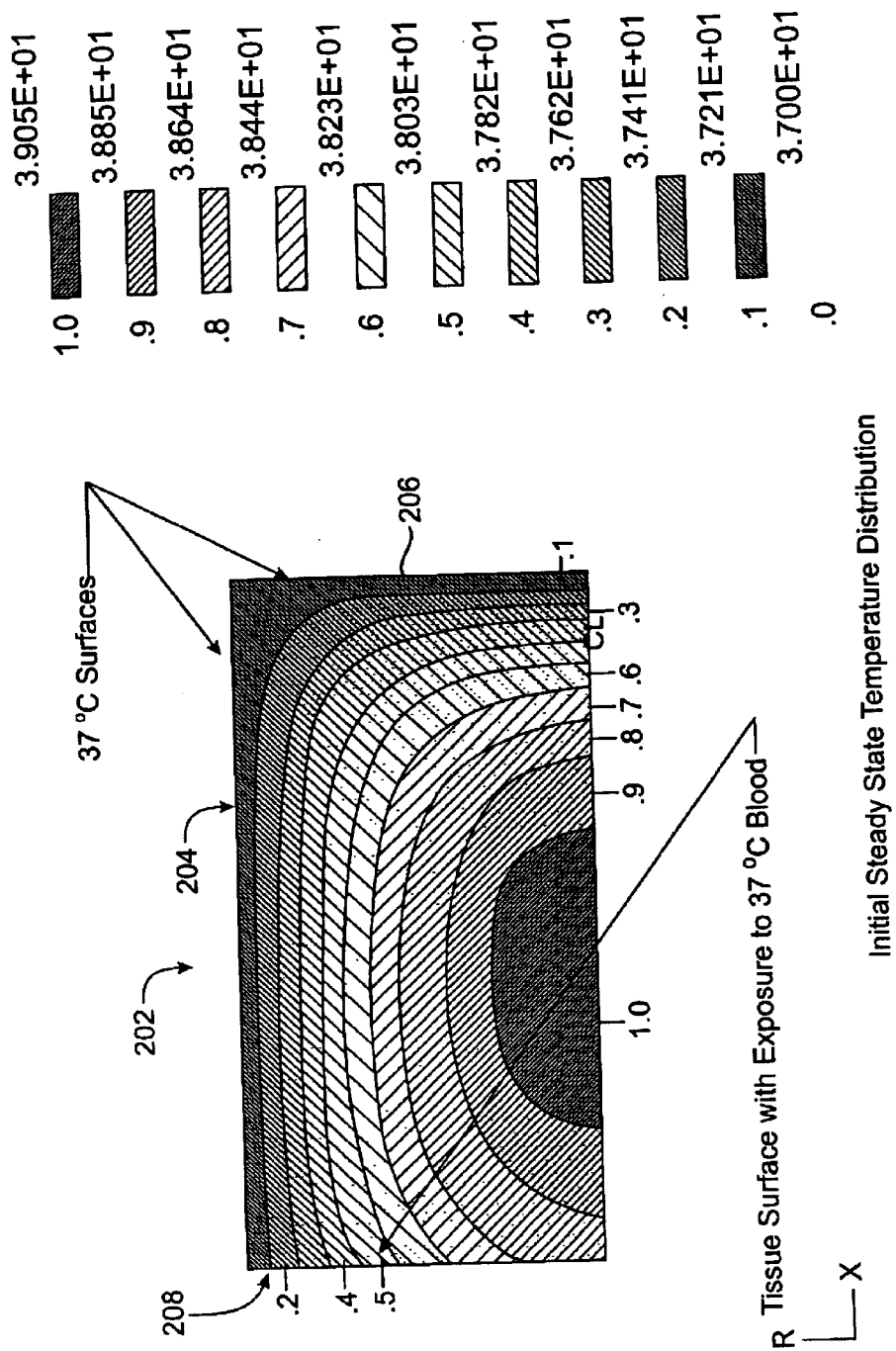
FIGS. 16A–16C are steady-state initial temperature distributions of the hot plaque thermal model of FIGS. 15A and 15B, a temperature distribution of the hot plaque thermal 30 seconds after engagement with a balloon filled by 35° C. water, and a temperature distribution of the hot plaque 30 seconds after engagement by a balloon filled with 35° C. gas, respectively.

Referring now to FIGS. 15A and 16A, the internal metabolic heating rate to achieve an average hot plaque luminal surface temperature of 38° C. may be determined based on thermal model 200. The 38° C. average hot plaque luminal surface temperature is based on published hot plaque characteristics. As illustrated in FIG. 16A, the steady state internal temperature distribution is hottest at the core of hot plaque 202 due to heat removal from the circumferential surface 204, the tissue engaging end 206, and the luminal surface 208. Hot plaque luminal surface temperatures may be measured using a thermocouple, a fiber optic cable connected to an infrared detector, resistance temperature detectors, or the like.

Figure 16B:
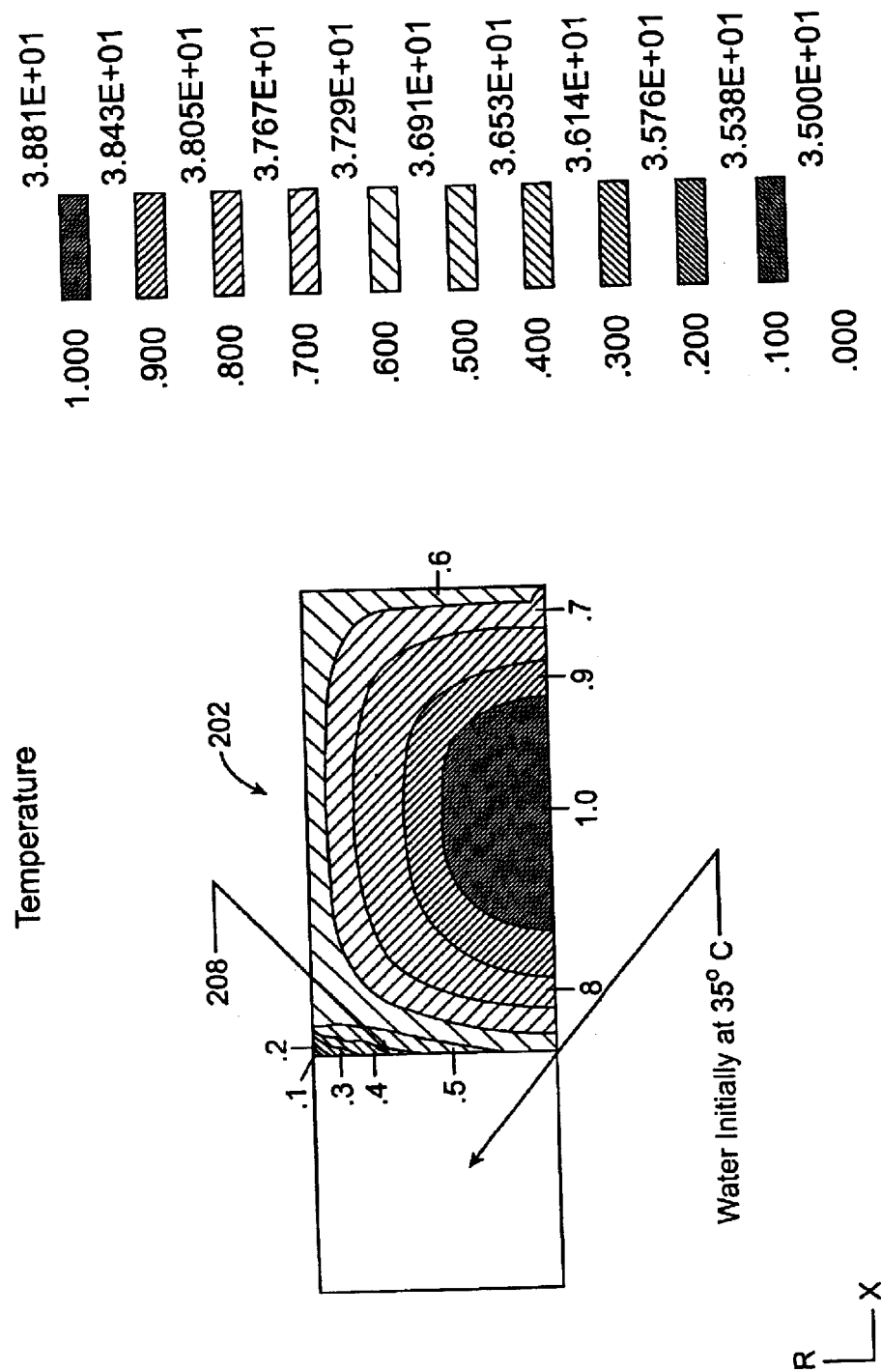

Referring now to FIGS. 15B and 16B and C, once the metabolic heating rate of hot plaque 202 has been identified using thermal model 200, the thermal model may be modified to include one or more balloon walls disposed between luminal surface 208 and a balloon inflation fluid 210. In the exemplary thermal model, the luminal hot plaque surface 208 was assumed to be covered by first and second layers of PET 212, 214. Each layer was modeled as having a thickness of 0.0075 mm. Clearly, alternative single or multiple layer balloon structures might also be modeled by changing the thermal properties, thicknesses, or materials of the layers disposed between the hot plaque and the balloon inflation fluid.

The fluid 210 of the thermal model 200 within the balloon was assumed to be water or nitrous oxide gas. Temperatures were assumed to be measured at a temperature sensor 216 disposed between balloon layers 212, 214, with the exemplary temperature sensor location being disposed at a radius of 0.583 mm from the hot plaque center so as to result in a starting surface temperature of approximately 38° C. Temperature of the temperature sensor versus time was determined (see FIGS. 17A–D) and internal and surface temperature distributions were computed after 30 seconds of thermal exposure.

Figure 16C:
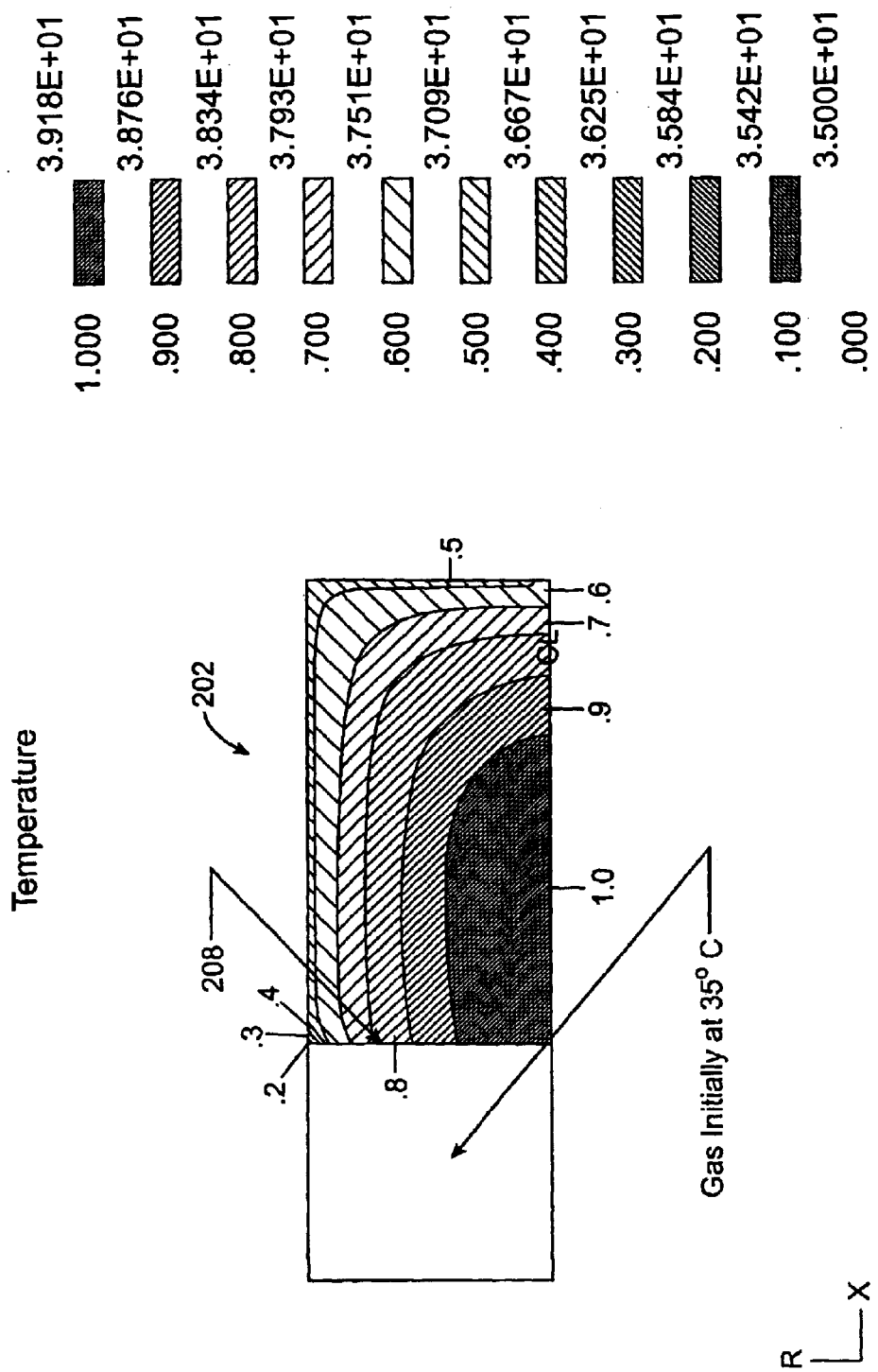

Referring now to FIGS. 16A–C, FIG. 16A graphically illustrates steady-state temperature distribution within the hot plaque prior to engagement by the balloon wall, thereby providing an initial temperature profile. FIG. 16B illustrates the hot plaque temperature distribution 30 seconds after thermal engagement by a balloon filled with 35° C. water. FIG. 16C shows hot plaque internal temperature distribution 30 seconds after exposure to a balloon filled with gas at 35° C. Qualitatively, it can be seen that the gas-filled balloon provides a temperature differential amplification along luminal tissue surface 208, as compared to the water-filled balloon. The region of the luminal wall having a measurably higher temperature is also larger for the gas-filled balloon than for the water-filled balloon, facilitating identification and locating of the hot plaque.

Referring now to FIGS. 17A–D, transient thermal analyses were made using the initial temperature distribution shown in FIG. 16A. Similar thermal analyses were performed for a tissue surface of a normal plaque, which is presumed to have a uniform temperature of 37° C. throughout. Transient tissue temperatures measured by a thermocouple 216 disposed between layers of a balloon 212, 214 are compared in FIG. 17A, with the graph illustrating measurement site temperatures times after engagement at a range of between a balloon filled with 37° C. gas or water at a normal tissue site and at a hot tissue (also referred to as a hot plaque or vulnerable plaque) site.

As would be expected, when a normal tissue site (having an initial temperature of 37° C.) is engaged by a balloon filled with water or nitrous oxide gas at 37° C., the temperature sensors indicates a constant 37° C. When a hot plaque is engaged with a water-filled balloon, the temperature sensor indicates an increasing temperature. While the initial surface of the hot plaque was 38° C., the reading from the water-filled balloon in FIG. 17A remains significantly less than 38° C., due to the heat transfer through the layers of the balloon wall to and from the water. As the heat transfers between the balloon wall and an internal gas is significantly less than that of a water-filled balloon, the hot tissue site as measured by a gas-filled balloon indicates a temperature difference of more than one degree between the hot tissue site and the normal tissue site. The gas-filled balloon acts as a thermal insulator on the hot tissue surface, allowing the measured temperature to rise beyond the initial hot tissue temperature. This surprising result can be understood with reference to FIG. 16A, and the above description of the thermal model of the hot plaque, once the metabolic heating (and associated cooling by the luminal blood flow) is considered. Hence, once a gas-filled balloon engages the hot plaque surface, the metabolic heating within the hot plaque and the insulating properties of the gas-filled balloon cause a signal amplification of the hot plaque indicating temperature differential.

Figure 17A:
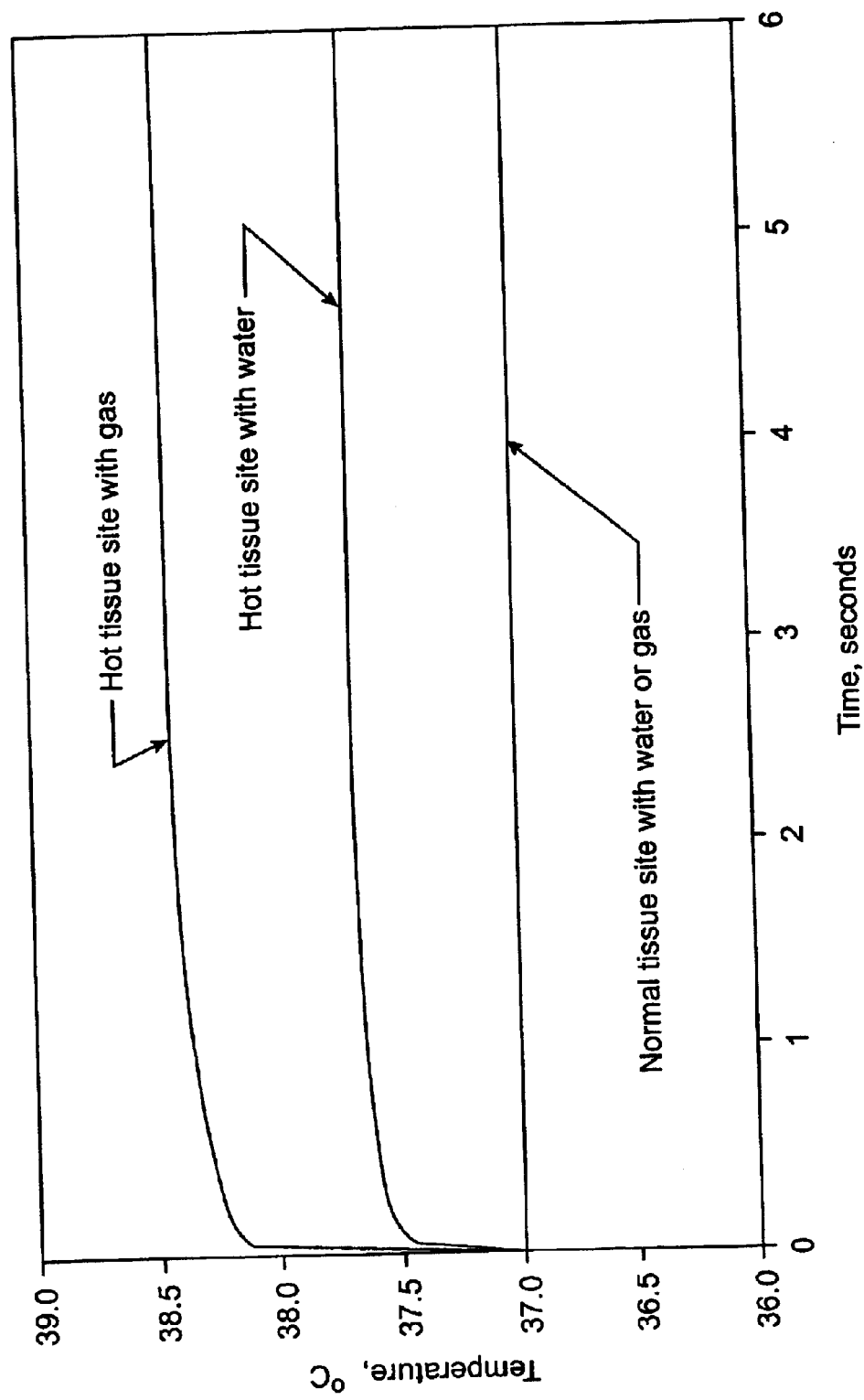
FIGS. 17A–17D graphically represent transient measurement temperatures with balloons having gas and liquid inflation fluids at differing temperatures.
Figure 17B:
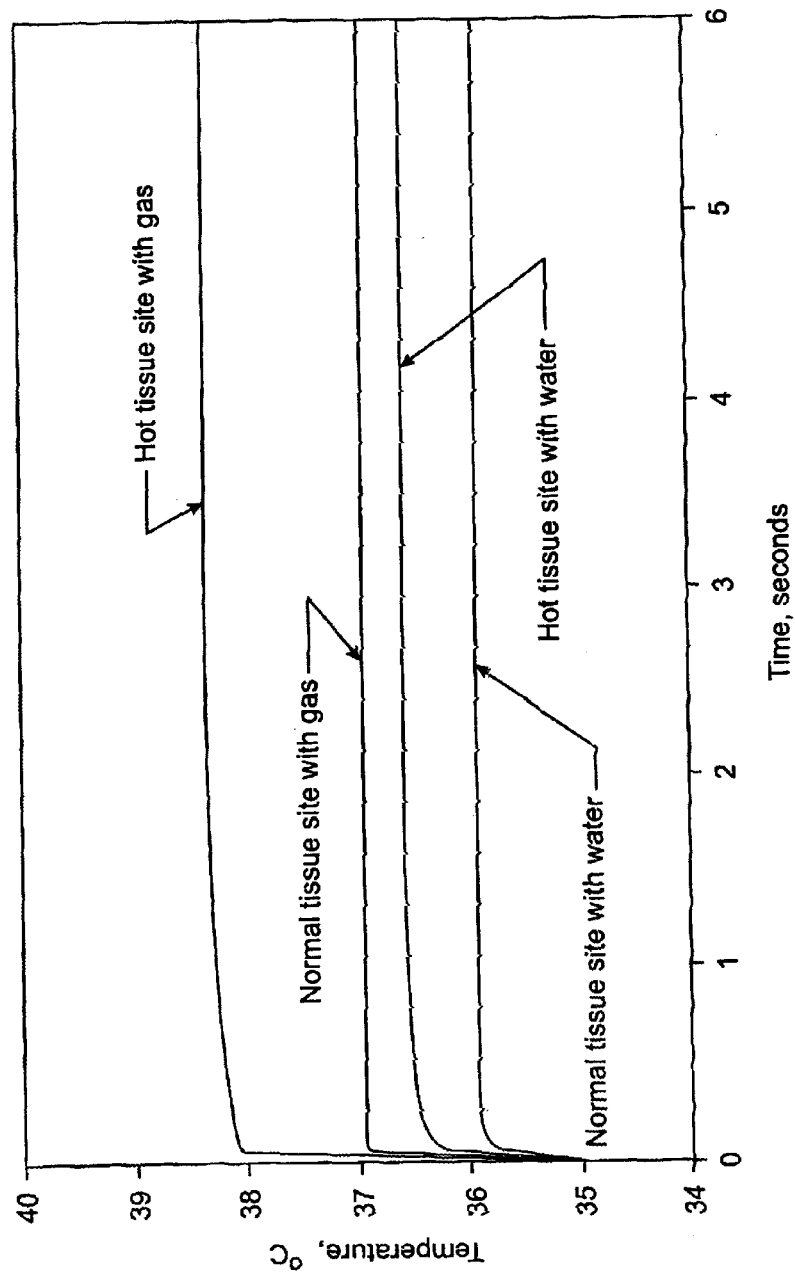
Figure 17C:
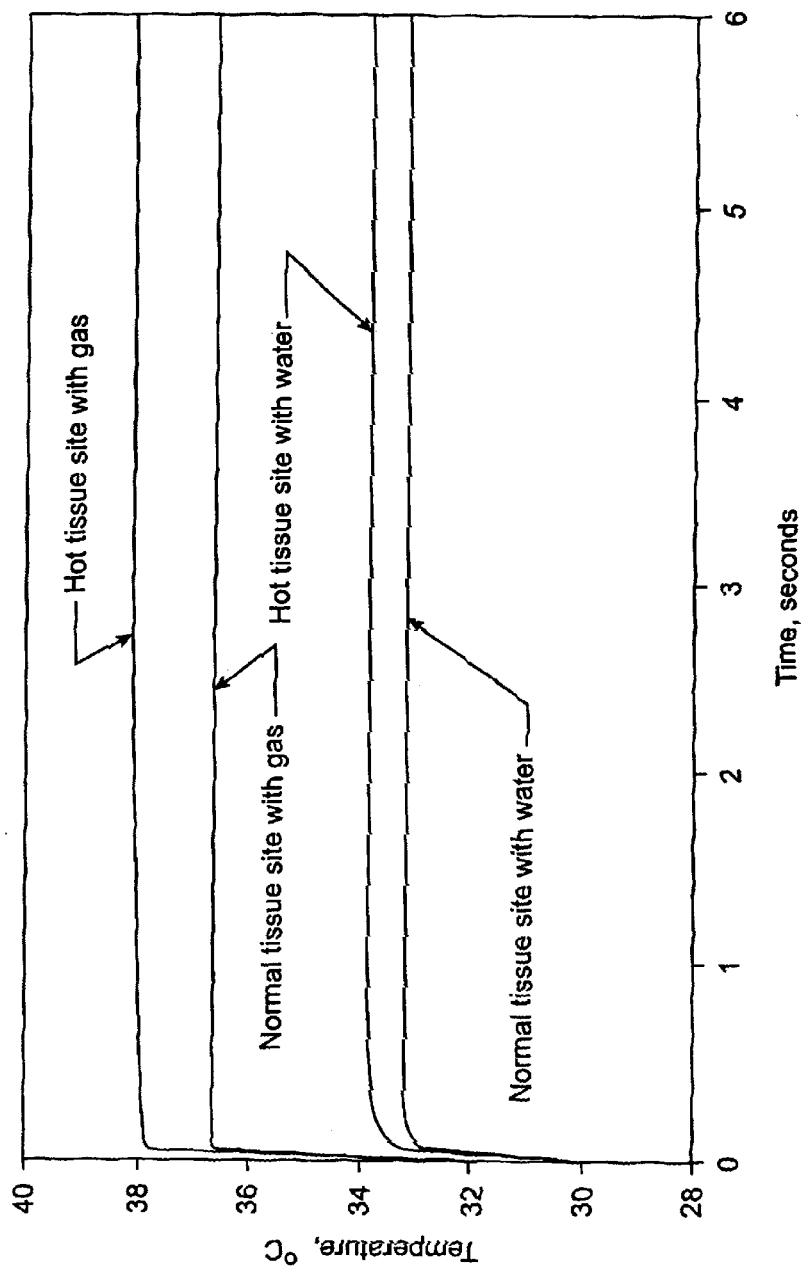
Figure 17D:
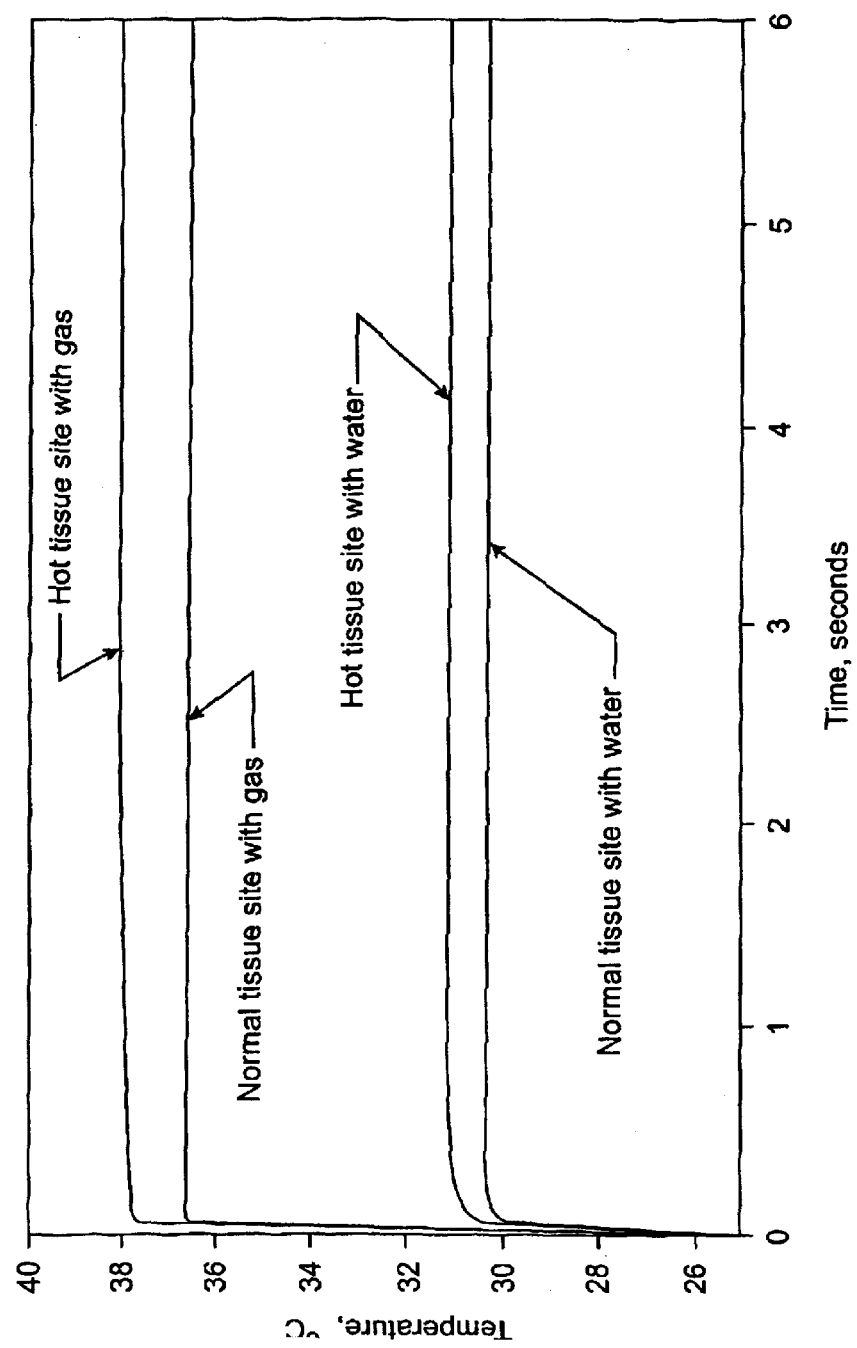

Referring now to FIGS. 17B, C, and D, the transient temperature response for balloons inflated with gases and liquids at temperatures of 35° C., 30° C., and 25° C., respectively, are provided. These figures indicate that the surface temperature differences between hot plaque and normal luminal tissues, as measured along the balloon wall, are approximately twice as large with a gas-filled balloon as they are with a liquid-filled balloon. Additionally, the maximum hot plaque surface temperature is generally greater with a gas-filled balloon than with a liquid-filled balloon, and the use of a gas-filled balloon actually amplifies the hot plaque surface temperature differential when the initial gas temperature is 30° C. or higher. Once again, this signal amplification results from the reduced heat transfer from the hot plaque into a gas-filled balloon as compared to the heat transfer to luminal blood flow and/or a liquid-filled balloon. This amplifying effect is not provided with a liquid-filled balloon.

In general, thermal model 200 indicates a greater different between hot plaque luminal surface temperatures and normal plaque or healthy luminal surface tissue temperatures after balloon inflation. A larger difference in these temperatures can result in a higher detection sensitivity. The absolute value of the surface temperature after balloon inflation was also evaluated, as higher surface temperatures also produce a higher differentiation sensitivity. Per both of these evaluation criteria, the gas-filled balloon performance exceeded that of the liquid-filled balloon performance particularly when relatively warm gases were used within the balloon. Specifically, under the thermal model analyses, the gas-filled balloon resulted in a higher difference between the measured hot plaque surface temperature and the measured normal plaque surface temperature, with the temperature differences using a gas-filled balloon being approximately twice those resulting from a liquid-filled balloon. Additionally, the absolute measured hot plaque surface temperature was uniformly higher when a gas-filled balloon was modeled as compared to a water-filled balloon.

While the above is a complete description of the preferred embodiments of the invention, various alternatives, modifications, and equivalents will be obvious to those of skill in the art. Hence, the above description should not be taken as limiting the scope of the invention which is defined by the appended claims.

What is claimed is:

1. A method for treating vulnerable plaque of a blood vessel, the vulnerable plaque releasably retaining fluid, said method comprising:
   identifying a portion of the vasculature for inhibiting release of the retained fluid;
   determining a plaque location is within the identified portion of the vasculature;
   introducing a catheter into a lumen of the blood vessel and positioning a balloon of the catheter within the vessel lumen adjacent the vulnerable plaque; and
   in response to the determining step, selectively cooling the vulnerable plaque at the plaque location to a temperature sufficient to inhibit release of the retained fluid into the blood vessel by introducing cooling fluid into the balloon of the balloon catheter so that the temperature of an outer surface of the balloon is in a range from about 10° C. to −40° C. for a time period in a range from about 15 to 120 seconds.

2. A method as in claim 1, further comprising differentiating the vulnerable plaque from standard stenotic plaque.

3. A method as in claim 2, wherein the differentiating step comprises sensing a temperature of a tissue adjacent the balloon while the balloon is inflated with a gas.

4. A method as in claim 3, wherein the differentiating step further comprises inflating the balloon so that a temperature of the gas within the balloon is at a first temperature, and wherein the cooling step comprises cooling an outer surface the balloon to a second temperature less than the first temperature.

5. A method as in claim 3, wherein the differentiating step further comprises inflating the balloon so that a temperature of the gas within the balloon is about 20° C. or more.

6. A method as in claim 1, wherein the blood vessel is an artery.

7. A method as in claim 1, wherein the fluid of the vulnerable plaque comprises a lipid-rich liquid, and wherein the vulnerable plaque comprises a cap of cells between the lipid-rich liquid and a lumen of the blood vessel.

8. A method as in clam 7, further comprising inhibiting apoptosis of tissue adjacent the lipid-rich liquid.

9. A method as in claim 8, wherein the cooling step inhibits rupture of the cap of cells.

10. A method as in claim 7, further comprising stabilizing the vulnerable plaque by cooling the lipid-rich liquid to a highly ordered hexagonal lattice.

11. A method as in claim 10, wherein the lipid-rich liquid is hardened to at least a gel-state.

12. A method as in claim 7, further comprising passivating the vulnerable plaque.

13. A method as in claim 12, wherein passivation comprises at least one of: reducing a size or modifying a consistency or composition of the lipid-rich liquid; altering the chemistry or life cycle of the vulnerable plaque; and increasing a thickness of the cap of cells.

14. A method as in claim 1, wherein the cooling inhibits inflammation of the vulnerable plaque or deterioration of the vulnerable plaque.

15. A method as in claim 1, further comprising treating the vulnerable plaque with at least one of angioplasty, stenting, and atherectomy.

16. A kit for treating vulnerable plaque of a blood vessel, the vulnerable plaque releasably retaining fluid, the kit comprising:
   a catheter having a proximal end, a distal end, and a cooling member; and
   instructions for use of the catheter according to claim 1.

17. A method for treating vulnerable plaque of a blood vessel, the vulnerable plaque releasably retaining fluid, said method comprising:

detecting the vulnerable plaque with a balloon catheter by inflating a balloon of the balloon catheter so that a gas within the balloon is at a temperature of about 30° C. or more; and cooling the vulnerable plaque, with the balloon catheter, to a temperature sufficient to inhibit release of the retained fluid into the blood vessel.

18. A method as in claim 17, wherein the cooling step comprises cooling an outer surface of the balloon to a temperature of about 10° C. or less.

19. A kit for detecting vulnerable plaque of a blood vessel, the kit comprising:

a catheter having a proximal end, a distal end, and a balloon member with a plurality of temperature sensors near its distal end; and instructions for use of the catheter according to claim 18.

* * * * *

UNITED STATES PATENT AND TRADEMARK OFFICE
CERTIFICATE OF CORRECTION

| | |
|---|---|
| PATENT NO. | : 6,955,174 B2 |
| APPLICATION NO. | : 10/387347 |
| DATED | : October 18, 2005 |
| INVENTOR(S) | : James Joye, Kristine Tatsutani and Joseph J. Williams |

Page 1 of 1

It is certified that error appears in the above-identified patent and that said Letters Patent is hereby corrected as shown below:

Title Page, item [73]: Assignee, please delete "Uryovascular Systems, Inc." and insert --CryoVascular Systems, Inc.--therefor.

Signed and Sealed this

Tenth Day of April, 2007

JON W. DUDAS
*Director of the United States Patent and Trademark Office*